United States Patent

Miyazawa et al.

[11] Patent Number: 5,723,472
[45] Date of Patent: Mar. 3, 1998

[54] AMINOBENZOIC ACID DERIVATIVES

[75] Inventors: Shuhei Miyazawa; Yorihisa Hoshino; Hisashi Shibata; Kazuo Hirota; Takaaki Kameyama; Shinya Abe; Takashi Yamanaka, all of Ibaraki, Japan

[73] Assignee: Eisai Co., Ltd., Tokyo, Japan

[21] Appl. No.: 806,536

[22] Filed: Feb. 24, 1997

Related U.S. Application Data

[62] Division of Ser. No. 458,038, Jun. 1, 1995, which is a division of Ser. No. 275,704, Jul. 18, 1994, Pat. No. 5,512, 579.

[30] Foreign Application Priority Data

Jul. 30, 1993 [JP] Japan ............... 5-189693

[51] Int. Cl.$^6$ ............... A61K 31/435; C07D 265/12; C07D 221/22
[52] U.S. Cl. ............... 514/294; 514/230.5; 514/299; 544/90; 546/79; 546/101; 546/112
[58] Field of Search ............... 514/230.5, 294, 514/299; 544/90; 546/79, 101, 112

[56] References Cited

U.S. PATENT DOCUMENTS

| | | | |
|---|---|---|---|
| 4,472,413 | 9/1984 | Hadley et al. | 546/112 |
| 5,256,671 | 10/1993 | Ladduwahetty et al. | 514/305 |
| 5,389,643 | 2/1995 | Miyazawa et al. | 514/304 |

FOREIGN PATENT DOCUMENTS

| | | |
|---|---|---|
| 0212802 | 3/1971 | European Pat. Off. |
| 0031219 | 7/1981 | European Pat. Off. |
| 0076530 | 4/1983 | European Pat. Off. |
| 0094742 | 11/1983 | European Pat. Off. |
| 0099194 | 1/1984 | European Pat. Off. |
| 0226267 | 6/1987 | European Pat. Off. |
| 0227215 | 7/1987 | European Pat. Off. |
| 0377967 | 7/1990 | European Pat. Off. |
| 0469449 | 2/1992 | European Pat. Off. |
| 0554794 | 8/1993 | European Pat. Off. |
| 2370731 | 6/1978 | France |
| 8502847 | 7/1985 | WIPO |
| 9212149 | 7/1992 | WIPO |

OTHER PUBLICATIONS

Chemical Abstracts, 120: 106775 (1993).

*Primary Examiner*—Yogendra N. Gupta
*Attorney, Agent, or Firm*—Birch, Stewart, Kolasch & Birch, LLP

[57] ABSTRACT

To provide a compound which exhibits a serotonin antagonism and an acetylcholine release accelerating activity at a well-balanced activity ratio. An aminobenzoic acid derivative represented by the general formula (I) or (II) or a pharmacologically acceptable salt thereof:

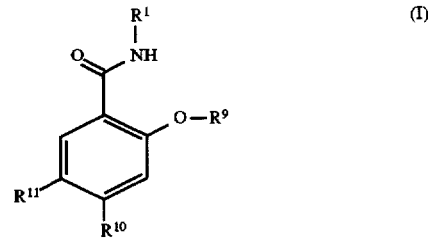

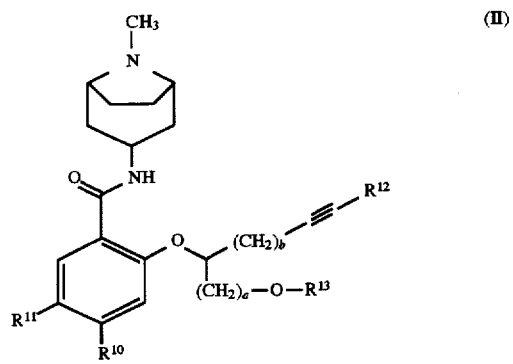

[wherein $R^1$ represents a group represented by the formula:

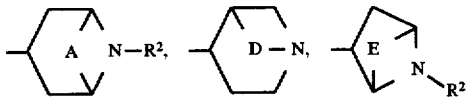

{wherein A represents a group represented by formula —$CH_2$—X—$CH_2$— (wherein X represents O, >N—$R^6$ or >$CHR^7$ (wherein $R^6$ represents lower alkyl and $R^7$ represents hydrogen or lower alkoxy)), etc.; D and E each represents a group represented by formula —$(CH_2)_3$—, etc., and $R^2$ represents lower alkyl, etc.}; $R^9$ represents alkynyl; $R^{10}$ represents amino, etc.; $R^{11}$ represents halogen; $R^{12}$ and $R^{13}$ each represent lower alkyl; a is an integer of 1 to 5; and b is an integer of 0 to 5].

9 Claims, No Drawings

AMINOBENZOIC ACID DERIVATIVES

This application is a divisional of copending application Ser. No. 08/458,038, filed on Jun. 1, 1995, which is a divisional of application Ser. No. 08/275,704 filed on Jul. 18, 1994, now U.S. Pat. No. 5,512,579, the entire contents of which are hereby incorporated by reference.

[FIELD OF INDUSTRIAL APPLICATION]

The present invention relates to an aminobenzoic acid derivative. More particularly, it relates to an aminobenzoic acid derivative useful as drugs.

[BACKGROUND OF THE INVENTION AND PRIOR ART]

The proportion of patients with indefinite complaints such as abdominal distension, heartburn, nausea and vomiting among those with gastrointestinal diseases has recently increased steadily and now reaches 60% or above.

Most of these indefinite complaints are caused by the functional anomaly of the digestive tract. For example, it is known that a patient with epigastric indefinite complaints such as chronic gastritis is in a state of delayed-gastric emptying, while a patient with hypogastric indefinite complaints such as irritable bowel syndrome including abnormal evacuation and abdominal pain as the cardinal symptom is in a state of intestinal hyperanakinezia.

It is ascertained that stress and anxiety are causative of any indefinite complaint, and in this sence, it is not too much to say that indefinite complaint is one of modern diseases.

Dopamine antagonists, musculotropic agents for regulating the movement of smooth muscles and acetylcholine release accelerators are now used in order to ameliorate the above gastrointestinal indefinite complaints. However, dopamine antagonists cause potent adverse reactions such as parkinsonism, so that they must be used carefully; musculotropic agents for regulating the movement of smooth muscles cause adverse reactions such as constipation unfavorably; and acetylcholine release accelerators do not effectively act as an antiemetic or anxiolytic, thus being unsatisfactory.

[SUMMARY OF THE INVENTION]

Under these circumstances, the inventors of the present invention have set about making studies for the purpose of developing a drug which is efficacious in treating all types of patients with gastrointestinal indefinite complaints without causing any potent adverse reaction and exhibits a depressant activity against anxiety which is nearly always found as one of the background factors of such patients.

As a result of the studies, it has been concluded that the above requirements can be fulfilled by a drug exhibiting both a serotonin (hereinafter abbreviated to "5-HT$_3$") antagonism and an acetylcholine (hereinafter abbreviated to "ACh") release accelerating activity. Therefore, further studies have been made in order to find a compound exhibiting both the activities at a well-balanced activity ratio to find out that the object can be attained by using an aminobenzoic acid derivative represented by the following general formula (I) or (II) or a pharmacologically acceptable salt thereof. The present invention has been accomplished on the basis of this finding.

Although aminobenzoic acid derivatives useful as drugs have been described in JP-B No. 29356/1986 and JP-A Nos. 36675/1984, 72886/1985, 226858/1985, 152628/1986, 161282/1986, 155277/1987 and 313757/1988, the compounds of the present invention are different from them in the chemical structures.

The compound of the present invention is an aminobenzoic acid derivative represented by the following general formula (I) or a pharmacologically acceptable salt thereof:

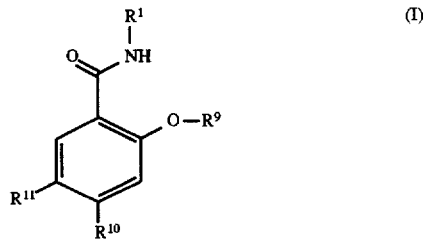

[wherein $R^1$ represents a group represented by the formula:

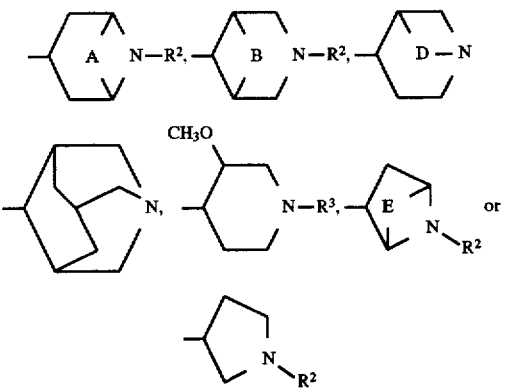

{wherein A and B may be the same or different from each other and each represents a group represented by formula —CH$_2$—X—CH$_2$— (wherein X represents O, >N—R$^6$ or >CHR$^7$ (wherein R$^6$ represents lower alkyl; and R$^7$ represents hydrogen or lower alkoxy) or a group represented by the formula:

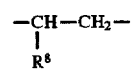

(wherein R$^8$ represents hydrogen, hydroxyl or lower alkoxy); D and E may be the same or different from each other and each represents a group represented by formula —(CH$_2$)$_3$— or a group represented by formula —O—(CH$_2$)$_2$—; R$^2$ represents hydrogen, lower alkyl or arylalkyl, provided that when R$^8$ is hydrogen, R$^2$ is not methyl; and R$^3$ represents hydrogen, lower alkyl, a group represented by formula —CO$_2$(CH$_2$)$_n$H (wherein n is an integer of 1 to 4) or a group represented by the formula:

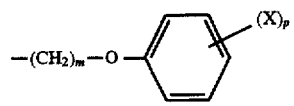

(wherein m is an integer of 1 to 4; X represents halogen, lower alkyl or lower alkoxy; and p is zero or an integer of 1 to 5)};

R$^9$ represents alkynyl;

R$^{10}$ represents amino, acylamino or alkylamino; and

R$^{11}$ represents halogen].

The invention provides a pharmacological composition comprising a pharmacologically effective amount of the compound as defined above or a pharmacologically acceptable salt thereof and a pharmacologically acceptable carrier.

The invention moreover provides a method for preventing or therapeutically treating a disease against which serotonin antagonism or an acetylcholine release accelerating action is efficacious by administering a pharmacologically effective amount of the compound to a subject who suffers or will suffer from the disease.

Further, the compound of the present invention is also an aminobenzoic acid derivative represented by the following general formula (II) or a pharmacologically acceptable salt thereof:

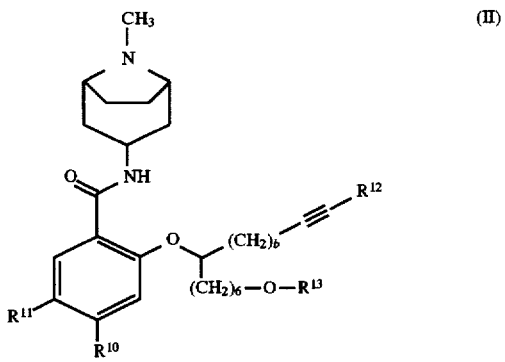

(wherein $R^1$ represents amino, acylamino or alkylamino; $R^{11}$ represents halogen; $R^{12}$ and $R^{13}$ each represent lower alkyl; a is an integer of 1 to 5, preferably 2; and b is an integer of 0 to 5, preferably 0).

In the general formulae (I) and (II), the lower alkyl defined with respect to $R^2$, $R^3$, $R^6$, $R^{12}$ and $R^{13}$ is a linear or branched one having 1 to 3 carbon atoms, such as methyl, ethyl, propyl or isopropyl. Further, the lower alkoxy defined with respect to $R^7$ and $R^8$ is methoxy, ethoxy, n-propoxy or isopropoxy. Furthermore, the arylalkyl defined with respect to $R^2$ is benzyl, phenylethyl, phenylpropyl or the like.

The alkynyl defined with respect to $R^9$ is preferably

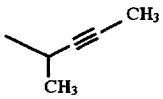

The acyl constituting the acylamino defined with respect to $R^{10}$ may be one derived from an aliphatic saturated carboxylic acid, an aliphatic unsaturated carboxylic acid, a saturated or unsaturated carbocyclic carboxylic acid, a heterocyclic carboxylic acid, a hydroxycarboxylic acid or any other carboxylic acid. Examples of the acyl include formyl, acetyl, propionyl, benzoyl, toluoyl, naphthoyl, furoyl and nicotinoyl.

Further, the alkyl constituting the alkylamino defined with respect to $R^{10}$ is as defined above with respect to the lower alkyl.

The halogen defined with respect to $R^{11}$ is chlorine, fluorine, bromine or the like.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as aspartate and glutamate.

Further, the compounds according to the present invention may be present as hydrates and the present invention includes these hydrates.

Although the compound of the present invention may be present as geometrical isomers or optical isomers, it is needless to say that the present invention includes all of the isomers. Further, the compound of the present invention may be any of S-, R- and RS-forms.

The compound according to the present invention exhibits a serotonin antagonism and an acetylcholine release accelerating activity and is therefore useful as a preventive and therapeutic agent for diseases against which these activities are efficacious. Further, the compound according to the present invention is useful also as an agent for increasing a gastrointestinal function, such as one for increasing a gastric emptying function, an antiemetic or an anxiolytic and as a preventive and therapeutic agent for irritable bowel syndrome.

In this specification, the term "serotonin antagonism" refers to 5-$HT_3$ antagonism. More precisely, the compound of the present invention selectively inhibits 5-$HT_3$ among serotonin antagonists. Further, the acetylcholine release accelerating action is guessed to be due to the function of 5-$HT_4$ as an agonist.

Among the compounds according to the present invention, those represented by the following structural formulae and pharmacologically acceptable salts thereof are preferable:

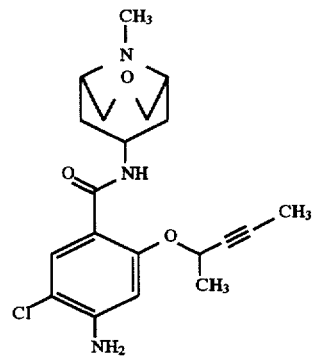

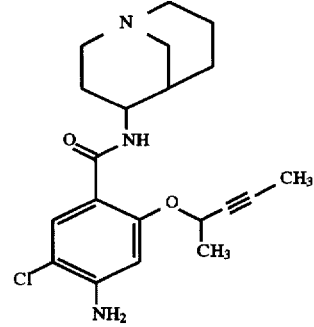

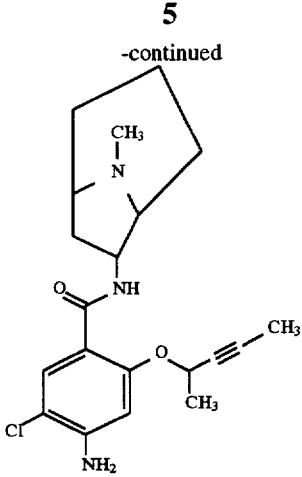

In particular, a compound represented by formula

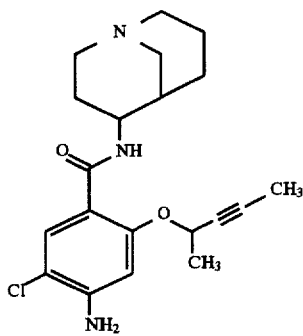

and pharmacologically acceptable salts thereof are still preferable.

Representative processes for preparing the compound of the present invention will now be described.

Preparation process 1

A compound represented by the general formula (I) wherein $R^{10}$ is amino can be prepared by the following process:

(Step 1)

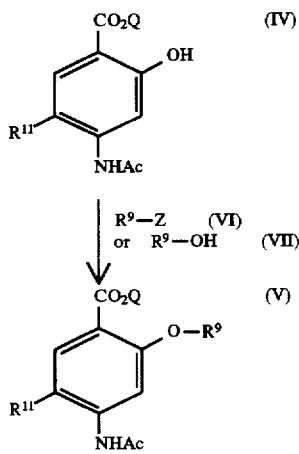

(wherein $R^9$ and $R^{11}$ are each as defined above; Q represents lower alkyl; Z represents halogen; and Ac represents acetyl)

In this step, a compound represented by the general formula (V) is prepared by reacting a compound represented by the general formula (IV) with a compound represented by the general formula (VI) or (VII).

In reacting the compound (IV) with the compound (VI), N,N-dimethylformamide, dimethyl sulfoxide or the like is preferably used as the solvent.

It is preferred that the reaction temperature range from 0° to 100° C., and the reaction time range from 30 minutes to 3 hours.

The reaction of the compound (IV) with the compound (VII) is conducted by reacting triphenylphosphine with an azodicarboxylate either in a solvent such as tetrahydrofuran or benzene or in the absence of any solvent in an inert gas atmosphere preferably at a temperature of −80° to 0° C., adding a solution of the compound (VII) in tetrahydrofuran and a solution of the compound (IV) therein to the obtained reaction mixture successively, and reacting the resulting mixture for 30 minutes to several hours while bringing the temperature to room temperature, thus giving a compound (V).

(Step 2)

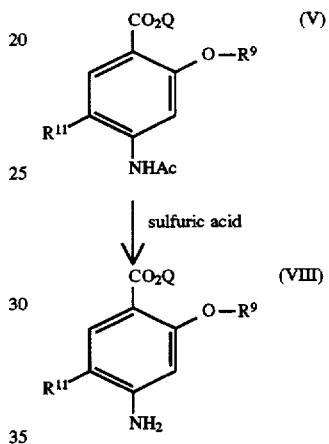

(wherein $R^9$, $R^{11}$, Q and Ac are each as defined above).

In this step, the compound (V) prepared in Step 1 is deacetylated. It is preferable that sulfuric acid be used in an equivalent amount or excess.

The solvent to be used in the reaction is particularly preferably an alcoholic solvent such as methanol or ethanol.

The reaction temperature preferably ranges from about 0° to 50° C.

(Step 3)

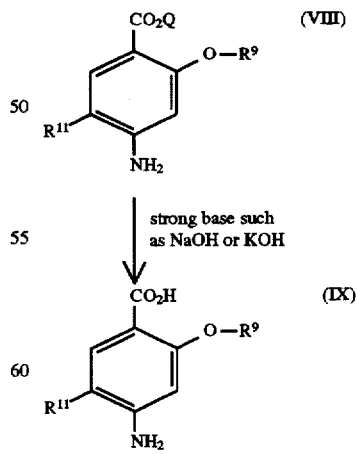

(wherein $R^9$, $R^{11}$ and Q are each as defined above)

In this step, the compound (VIII) prepared in Step 2 is hydrolyzed.

The hydrolysis is conducted in the presence of two or more equivalents of a strong base such as sodium hydroxide or potassium hydroxide in an alcoholic solvent such as methanol or ethanol at room temperature to 100° C. for several hours, by which a compound (IX) is obtained.

(Step 4)

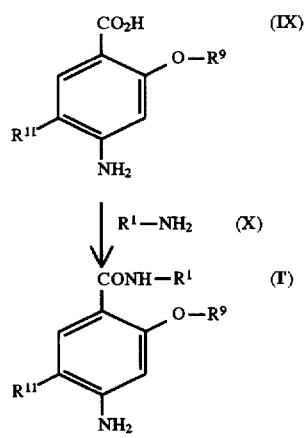

(wherein $R^1$, $R^9$ and $R^{11}$ are each as defined above).

In this step, a compound (I') is prepared by condensing the compound (IX) prepared in Step 3 with an amine (X) having an $R^1$ moiety.

The amine (X) can be prepared by, e.g., the process disclosed in JP-A No. 202890/1990, 18885/1983 or 30785/1987 or EP-A 0469449. The condensation is conducted in the presence of a suitable dehydrating agent, for example, a carbodiimide such as dicyclohexylcarbodiimide. Alternatively, it may be conducted by converting the compound (IX) into a conventional reactive derivative thereof such as an acid anhydride, a mixed acid anhydride, an acid azide, an active ester thereof with N-hydroxybenzotriazole, N-hydroxysuccinimide or the like, or acid chloride, and reacting the derivative with the amine (X). When the condensation is conducted through a mixed acid anhydride, the mixed acid anhydride may be one prepared by the use of a chlorocarbonic acid ester such as methyl chlorocarbonate, ethyl chlorocarbonate or phenyl chlorocarbonate.

These reactions may be conducted either in the absence of any solvent or in the presence of a solvent inert to the reactions, e.g., benzene, toluene, xylene, tetrahydrofuran, chloroform, carbon tetrachloride, N,N-dimethylformamide or pyridine.

When the reaction is conducted in a solvent, the simultaneous use of an inorganic base such as sodium hydrogencarbonate, potassium carbonate, sodium carbonate or sodium hydroxide or an organic base such as trimethylamine or pyridine gives more desirable results.

Preparation process 2

A compound represented by the general formula (I) wherein $R^{10}$ is amino can be prepared also by the following process:

(Step 1)

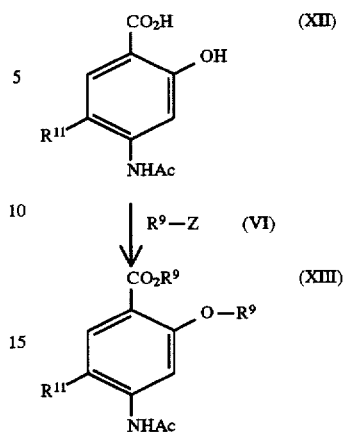

(wherein $R^9$, $R^{11}$, Z and Ac are each as defined above).

In this step, a compound represented by the general formula (XIII) is prepared by reacting a compound represented by the general formula (XII) with a compound represented by the general formula (VI) in the presence of a base for several hours.

The base is preferably potassium carbonate or sodium carbonate, though any base is usable in this step.

The solvent to be used in the reaction may be any one inert to the reaction.

The reaction temperature preferably ranges from about 0° to 100° C.

(Step 2)

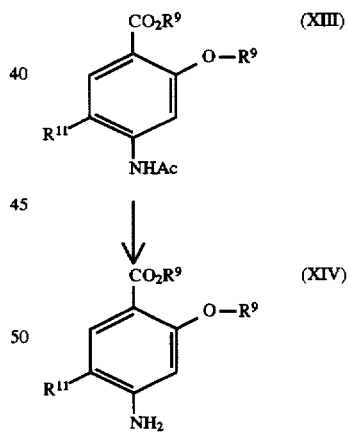

(wherein $R^9$, $R^{11}$ and Ac are each as defined above).

In this step, the compound (XIII) prepared in Step 1 was deacetylated into a compound represented by the general formula (XIV).

The deacetylation is conducted in the conventional manner, e.g., by treating the compound (XIII) in a mixture comprising sulfuric acid in an equivalent amount or excess and a solvent such as methanol or ethanol for several hours.

The reaction temperature preferably ranges from about 0° to 50° C.

(Step 3)

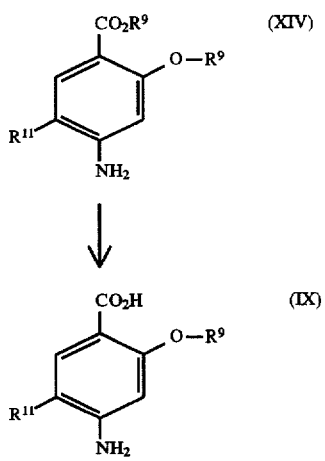

(wherein $R^9$ and $R^{11}$ are each as defined above).

In this step, the compound (XIV) prepared in Step 2 is hydrolyzed.

This hydrolysis is conducted in the conventional manner, for example, by treating the compound (XIV) in an alcoholic solvent such as methanol or ethanol in the presence of two or more equivalents of a strong base such as sodium hydroxide or potassium hydroxide at a temperature ranging from room temperature to 100° C. for several hours.

(Step 4)

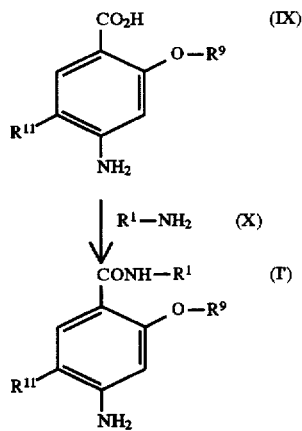

(wherein $R^1$, $R^9$ and $R^{11}$ are each as defined above).

In this step, the objective compound (I') is prepared in the same manner as that of Step 4 of Preparation process 1.

A compound represented by the general formula (I) wherein $R^{10}$ is a group other than amino can be prepared by, for example, a process which comprises converting the amino group of the compound (VIII) into an acylamino or alkylamino group through acylation or alkylation, hydrolyzing the resulting compound, and condensing the hydrolysate with a tropane or a tropine.

Experimental Examples will now be described to illustrate the effects of the compounds according to the present invention in detail.

[EXPERIMENTAL EXAMPLE 1]

Antagonism against 2-methyl-serotonin-induced contraction of ileum (serotonin 3 antagonism)

This experiment was made according to the method of Sanger et al. [see Eur. J. Pharmacol., 159, 113–124 (1989)].

The nonterminal ileum of a Hartley male guinea pig was suspended in the Krebs solution (37° C.) by applying a load of 0.5 g, and a gaseous mixture comprising 95% of oxygen and 5% of carbon dioxide was passed through the solution. The contraction of the ileum was isometrically determined. After allowing the ileum to stand for one or more hours for stabilization, a solution of a test compound was added to the solution, and after 30 minutes, 2-methyl-serotonin was noncumulatively added. The pA2 value was calculated from the rightward shift of the dose-response curve of the 2-methylserotonin-induced contraction caused by the test compound according to the method of Rossum et al. [see Arch. Int. Pharmacodyn. 143, 299(1963)]. BRL 24924 (Renzapride) was used as a control in this experiment.

The structural formula of BRL 24924 is as follows:

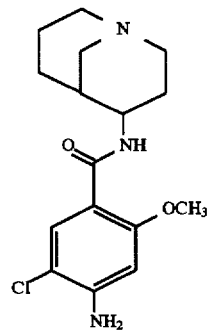

The results are given in Table 1.

TABLE 1

| Test compd. (Ex. compd.) | pA2 |
|---|---|
| 6 | 7.7 |
| 20 fraction 1 | 7.2 |
| 20 fraction 2 | 7.9 |
| 31 fraction 1 | 7.2 |
| 31 fraction 2 | 8.3 |
| 53 fraction 2-1 | 8.6 |
| 53 fraction 2-2 | 7.9 |
| BRL 24924 (Renzapride) | 6.6 |

[EXPERIMENTAL EXAMPLE 2]

Activity against cisplatin-induced vomiting of beagle

Beagles weighing 7 to 12 kg were used. 3 mg/kg of cisplatin (a product of Sigma) (1 ml/kg of physiological saline) was administered to each beagle through the vein of one of its forefeet. One hour after the administration, physiological saline (0.2 ml/kg) was administered to a control group of beagles and a solution of a test compound in physiological saline was administered to a test group of beagles, each through the vein of the other forefoot. The frequency of vomiting observed over a 5-hour period from the administration of cisplatin was recorded and the inhibitory ratio of the test compound was calculated according to the following formula.

The results are given in Table 2.

$$\text{inhibitory ratio (\%)} = \left[1 - \frac{\text{average frequency of test group}}{\text{average frequency of control group}}\right] \times 100$$

TABLE 2

| Test compd. | Inhibitory ratio against cisplatin-induced vomiting (%) | |
|---|---|---|
| (Ex. compd.) | 0.03 mg/kg | 0.1 mg/kg |
| 2 | 14 | 53 |
| 6 |  | 77 |
| 20 fraction 1 |  | 22 |
| 20 fraction 2 | 14 | 24 |
| 31 fraction 2 | 63 | 92 |
| BRL 24924 (Renzapride) | 19 | 61 |

[EXPERIMENTAL EXAMPLE 3]

Activity for increasing gastric emptying function

This experiment was made according to the method of Decktor et al. [see Eur. J. Pharmacol., 313–316 (1988)]. Fischer male rats (weight: 160 to 180 g) were fasted for 18 hours before 3 ml of a test food comprising methylcellulose, beef bouillon, casein, sugar and corn starch was orally administered to each rat. One hour after the administration, the stomach was extirpated from each rat. The gastric emptying ratio was calculated from the weight of the test food remaining in the stomach. The percentage increment of the gastric emptying function was determined by comparing the gastric emptying ratio of a medicated rat with that of a control rat. Each test compound (5 ml/kg) was orally administered one hour before the administration of the test food. BRL 24924 was used as a control in this experiment.

The results are given in Table 3.

TABLE 3

| | Percentage increment of gastric emptying function (%) | | | | |
|---|---|---|---|---|---|
| Test compd. (Ex compd.) | 0.01 mg/kg | 0.03 mg/kg | 0.1 mg/kg | 0.3 mg/kg | 1 mg/kg |
| 2 | 20.5* | 19.7 | 19.8 | 30.6 | |
| 15 | | 24.6* | 30.6 | | |
| 20 fraction 1 | 3.9 | 8.9 | 22.9* | 11.5 | |
| 20 fraction 2 | | 14.0 | 23.3* | 21.8 | |
| 31 fraction 1 | | 0.8 | 0.8 | 14.1* | |
| 31 fraction 2 | 4.5 | 24.6* | 25.8 | 33.2 | |
| 53 fraction 2 | | | 14.4* | 16.1 | |
| 53 fraction 2-1 | 14.4 | 22.2* | 26.7 | 29.0 | |
| 53 fraction 2-2 | | 6.6 | 21.3* | 28.8 | |
| BRL 24924 (Renzapride) | | | 1.9 | 6.5 | 18.5* |

TABLE 3-continued

| | Percentage increment of gastric emptying function (%) | | | | |
|---|---|---|---|---|---|
| Test compd. (Ex compd.) | 0.01 mg/kg | 0.03 mg/kg | 0.1 mg/kg | 0.3 mg/kg | 1 mg/kg |

*minimum effective dose

[EXPERIMENTAL EXAMPLE 4]

Effect of relaxing the contraction of muscular layer of esophageal mucosa of rat by stimulation with carbachol (activity of serotonin 4 as agonist)

This experiment was made according to the method of Baxter et al. [see Naunyn-Schmiedeberg's Arch. Pharmacol., 343, 439–446 (1991)]. The esophagus of a rat was extirpated and freed from the outer tunica propria to obtain the muscular layer of mucosa. This sample was suspended in the Krebs-Henseleit solution kept at 37° C., while a gaseous mixture comprising 95% of $O_2$ and 5% of $CO_2$ was passed through the solution. A load of 0.5 g was applied to each sample and the reaction was recorded isometrically. 1 μM of carbachol was added to each sample to cause contraction, followed by the cumulative addition thereto of a solution of a test compound. The effect of the test compound was determined as the ratio (4) of relaxation based on the maximum contraction caused by carbachol. Table 4 shows the concentrations of test compounds at which the maximum contraction caused by carbachol is relaxed by 50%.

TABLE 4

| Test compd (Ex. compd.) | Effect of relaxing the muscular layer of esophageal mucosa of rat $EC_{50}$ (μM) |
|---|---|
| 2 | 0.082 |
| 4 | 1.3 |
| 6 | 0.11 |
| 15 | 0.035 |
| 35 | 2.0 |
| 42 | 6.2 |
| 44 | 0.11 |
| 50 | >10 |
| 19 | >10 |
| 20 fraction 1 | 0.060 |
| 20 fraction 2 | 0.033 |
| 28 fraction 1 | >10 |
| 28 fraction 2 | >10 |
| 29 | >10 |
| 31 fraction 1 | 0.044 |
| 31 fraction 2 | 0.19 |
| 53 fraction 2 | 0.31 |
| 53 fraction 2-1 | 0.30 |
| 53 fraction 2-2 | 0.18 |
| 55 | 0.64 |
| BRL 24924 (Renzapride) | 0.30 |

It can be understood from the results of the above pharmacological experiments that the compound of the present invention has a 5-HT$_3$ antagonism and an ACh release accelerating activity and is therefore effective in increasing the gastrointestinal functions such as gastric emptying function and useful as an antiemetic.

It has been ascertained by recent studies that an ACh release accelerating action is due to the action of 5=HT$_4$ as an agonist. Therefore, it is guessed that the increase of a gastrointestinal function by the compound according to the present invention may be influenced by such mechanism variously.

Accordingly, the compound of the present invention acts as a 5-HT$_3$ antagonist and an ACh release accelerator and hence is useful as a drug based on these activities.

The compound of the present invention is efficacious in the prevention and treatment of various diseases and specific examples of the diseases include irritable bowel syndrome; reflux esophagitis; gastrointestinal symptoms (such as heartburn, anorexia, nausea, vomiting, abdominal pain and abdominal distension) caused by chromic gastritis, gastroptosis, postgastrectomy syndrome or the like; gastrointestinal symptoms and gastrointestinal insufficiency represented by those caused by the administration of an anticancer drug or irradiation with radiation; anxiety; migraine; amenestic syndrome; senile dementia; Alzheimer disease; and dependence. In particular, the compound of the present invention is excellent in the balance between 5-HT3 antagonism and ACh release accelerating activity, so that it is extremely efficacious against gastrointestinal symptoms and gastrointestinal insufficiency.

Further, the compound of the present invention is less toxic and highly safe, thus being valuable also in this sense.

The compound of the present invention is administered as a therapeutic and preventive agent for the above diseases in the form of tablet, powder, granule, capsule, syrup or inhalant. Although the dose thereof remarkably varies depending upon the extent of symptom, age, and the kind of disease, the dose per adult a day is generally about 0.01 to 1000 mg, preferably 0.1 to 500 mg, still preferably 0.1 to 100 mg, which is administered in one to several portions a day.

When the compound of the present invention is administered as an injection, the dose is generally 1 to 3000 µg/kg, preferably about 3 to 1000 µg/kg.

The pharmaceutical preparations according to the present invention are prepared by the use of the conventional carriers in the conventional manner.

More precisely, a solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, menthol, aromatic powder, mentha oil, borneol and powdered cinnamon bark. Of course, the tablet and granule may be suitably coated with sugar, gelatin or the like, if necessary.

An injection according to the present invention is prepared by adding a pH regulator, buffer, stabilizer and/or solubilizing agent to an active ingredient at need and formulating the mixture into an injection for subcutaneous, intramuscular or intravenous administration by the conventional technique.

[EXAMPLE]

Examples according to the present invention will now be described, though it is needless to say that the present invention is not limited to them.

EXAMPLE 1

(S)-N-(9-Methyl-3-oxa-9-azabicyclo[3.3.1]non-7α-yl)-4-amino-5-chloro-2-(1-methyl-2-butynyl) oxybenzyamide

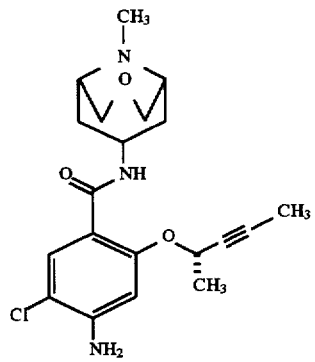

Ethyl chloroformate (0.54 g) was dropped into 30 ml of a dichloromethane solution of 1.0 g of (S)-4-amino-5-chloro-2-(1-methyl-2-butynyl)oxybenzoic acid and 0.8 g of triethylamine under cooling with ice. The obtained mixture was stirred at room temperature for 10 minutes, followed by the addition thereto of 1.37 g of 3α-amino-9-methyl-3-oxa-9-azabicyclo[3.3.1]nonane dihydrochloride. The obtained mixture was stirred overnight and a saturated aqueous solution of sodium hydrogencarbonate was poured into the reaction mixture. The obtained mixture was extracted with dichloromethane twice. The combined organic phases were dried over magnesium sulfate and freed from the solvent. The residue was purified by silica gel column chromatography (5 to 10% methanol/dichloromethane) to give 1.20 g of the title compound.

$^1$H-NMR (400 MHz, CDCl$_3$) δ ppm:

1.44–1.52(m, 2H), 1.55(d, J=7 Hz, 3H), 1.83(d, J=2 Hz, 3H), 2.44–2.54(m, 2H), 2.53(s, 3H), 2.63–2.67(m, 2H), 3.78–3.82(m, 2H), 3.90–3.96(m, 2H), 4.30(br.s, 2H), 4.72–4.79(m, 1H), 4.84–4.91(m, 1H), 6.48(s, 1H), 8.03 (s, 1H), 8.88(d, J=8 Hz, 1H)

EXAMPLE 2

(S)-N-(9-Methyl-3-oxa-9-azabicyclo[3.3.1]non-7α-yl)-4-amino-5-chloro-2-(1-methyl-2-butynyl)oxybenzamide hydrochloride

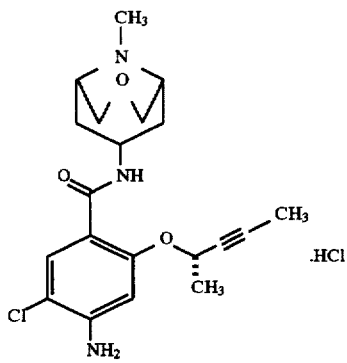

1.20 g of the (S)-N-(9-methyl-3-oxa-9-azabicyclo[3.3.1]non-7α-yl)-4-amino-5-chloro-2-(1-methyl-2-butynyl)oxybenzamide prepared in the Example 1 was dissolved in 3.10 ml of 1N hydrochloric acid, followed by the dilution thereof with distilled water. The resulting solution was freeze-dried to give 1.24 g of the title compound.

$^1$H-NMR (400 MHz, $d_6$-DMSO) δ ppm:
1.58(d, J=7 Hz, 3H), 1.63–1.71, 1.84–1.92(m×2, 2H), 1.80, 1.81 (d×2, J=2 Hz, 3H), 2.51–2.65(m, 1H), 2.70–2.85(m, 1H), 2.82, 2.95(d×2, J=2 Hz, 3H), 3.30–3.50(m, 2H), 3.73–3.84, 3.92–4.02(m×2, 2H), 4.30–4.48(m, 2H), 4.49–4.60(m, 1H), 4.97–5.03(m, 1H), 6.57(s, 1H), 7.72(s, 1H), 8.55, 8.58(d×2, J=8 Hz, 1H), 10.90, 11.35(br.s×2, 1H)
MS m/z (FAB): 392 (M$^+$+1)

EXAMPLE 3

(S)-N-(9-Methyl-9-azabicyclo[3.3.1]non-3α-yl)-4-amino-5-chloro-2-(1-methyl-2-butynyl)oxybenzamide

[Chemical formula 26]

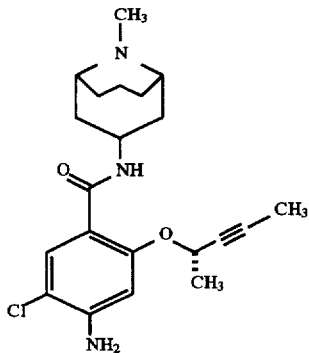

The title compound was prepared in a similar manner to that of the Example 1.

$^1$H-NMR (400 MHz, CDCl$_3$) δ ppm:
1.05–1.12(m, 2H), 1.23–1.34(m, 2H), 1.40–1.55(m, 2H), 1.68(d, J=7 Hz, 3H), 1.73–2.02(m, 2H), 2.45–2.60(m, 2H), 2.51(s, 3H), 3.05–3.12(m, 2H), 4.36(br.s, 2H), 4.37–4.47(m, 1H), 4.82–4.88(m, 1H), 6.46(s, 1H), 7.65 (d, J=7 Hz, 1H), 8.10(s, 1H)

EXAMPLE 4

(S)-N-(9-Methyl-9-azabicyclo[3.3.1]non-3α-yl)-4-amino-5-chloro-2-(1-methyl-2-butynyl)oxybenzamide hydrochloride

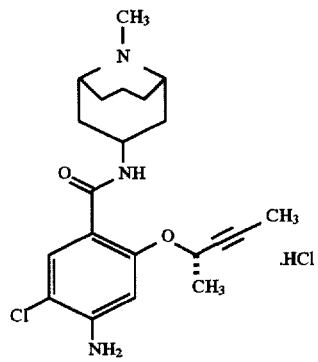

The title compound was prepared in a similar manner to that of the Example 2.

$^1$H-NMR (400 MHz, $d_6$-DMSO) δ ppm:
1.35–2.30(m, 8H), 1.60(d, J=7 Hz, 3H), 1.82(s, 3H), 2.44–2.92(m, 2H), 2.75(s, 3H), 3.45–3.72(m, 2H), 4.16–4.50(m, 1H), 4.90–5.08(m, 1H), 6.02, 6.04(s×2, 1H), 6.99, 7.04(s×2, 1H), 7.70, 7.87(d×2, J=7 Hz, 1H), 9.92, 10.91(br.s×2, 1H)
MS m/z (FAB): 390 (M$^+$+1)

EXAMPLE 5

N-(1-Azabicyclo[3.3.1]non-4α-yl)-4-amino-5-chloro-2-((S)-1-methyl-2-butynyl)oxybenzamide

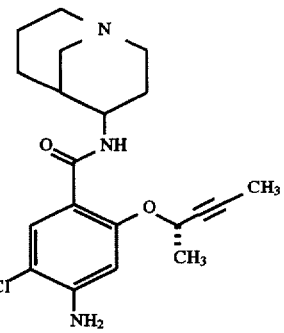

The title compound was prepared in a similar manner to that of the Example 1.

$^1$H-NMR (400 MHz, CDCl$_3$) δ ppm:
0.90–1.10(m, 1H), 1.35(d, J=7 Hz, 3H), 1.70–2.10(m, 6H), 1.70, 1.72(d×2, J=2 Hz, 3H), 2.94–3.22(m, 6H), 4.36(s, 2H), 4.40–4.52(m, 1H), 4.88–4.92(m, 1H), 6.48, 6.50(s×2, 1H), 7.84, 7.88(d×2, J=6 Hz, 1H), 8.11(s, 1H)

EXAMPLE 6

N-(1-Azabicyclo[3.3.1]non-4α-yl)-4-amino-5-chloro-2-((S)-1-methyl-2-butynyl)oxybenzamide hydrochloride

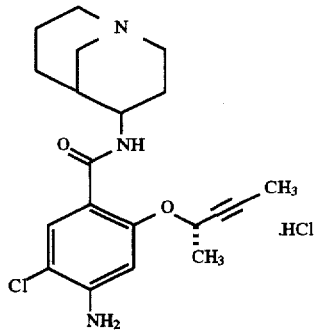

The title compound was prepared in a similar manner to that of the Example 2.

$^1$H-NMR (400 MHz, d$_6$-DMSO) δ ppm:

1.59(d, J=7 Hz, 3H), 1.64–1.92(m, 3H), 1.81, 1.82(d×2, J=2 Hz, 3H), 1.97–2.14(m, 3H), 2.17–2.23(m, 1H), 3.36–3.45(m, 6H), 4.30–4.40(m, 1H), 4.97–5.06(m, 1H), 6.62(s, 1H), 7.60(s, 1H), 7.78–7.85(m, 1H), 10.85 (br.s, 1H)

MS m/z (FAB): 376 (M$^+$+1)

EXAMPLE 7 cis-N-(1-Ethoxycarbonyl-3-methoxy-4-piperidinyl)-4-amino-5-chloro-2-((S)-1-methyl-2-butynyl)oxybenzamide

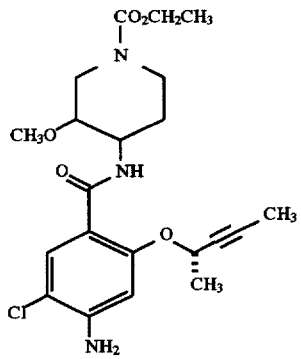

The title compound was prepared in a similar manner to that of the Example 1.

$^1$H-NMR (400 MHz, CDCl$_3$) δ ppm:

1.26(t, J=7 Hz, 3H), 1.68, 1.70(d×2, J=7 Hz, 3H), 1.72–1.78(m, 2H), 1.82, 1.83(d×2, J=2 Hz, 3H), 2.77–3.00(m, 2H), 3.34–3.47(m, 4H), 4.02–4.32(m, 5H), 4.37(br.s, 2H), 4.80–4.87(m, 1H), 6.48, 6.50(s×2, 1H), 8.08, 8.10(s×2, 1H), 8.15–8.26(m, 1H)

MS m/z (FAB): 438 (M$^+$+1)

EXAMPLE 8 cis-N-(3-Methoxy-4-piperidinyl)-4-amino-5-chloro-2-((S)-1-methyl-2-butynyl)oxybenzamide

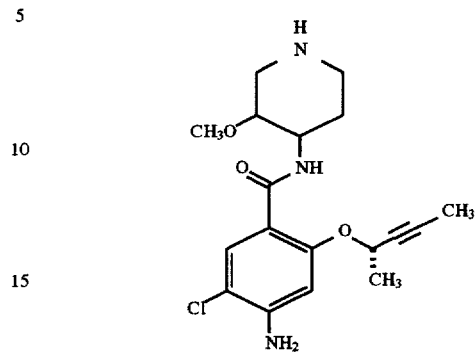

2.50 g of the cis-N-(1-ethoxycarbonyl-3-methoxy-4-piperidinyl)-4-amino-5-chloro-2-((S)-1-methyl-2-butynyl) oxybenzamide prepared in the Example 7 and 4.5 g of potassium hydroxide were dissolved in 2-propanol. The obtained solution was refluxed for 1.5 hours and cooled, followed by the addition thereto of water. The resulting mixture was extracted with 10% 2-propanol/chloroform thrice. The combined organic phases were dried over magnesium sulfate and freed from the solvent. The residue was purified by silica gel column chromatography (5 to 12% methanol/dichloromethane) to give 0.34 g of the title compound.

$^1$H-NMR (400 MHz, CDCl$_3$) δ ppm:

1.59–1.76(m, 2H), 1.68, 1.69(d×2, J=7 Hz, 3H), 1.79, 1.81(d×2, J=2 Hz, 3H), 1.58–2.73(m, 3H), 3.01–3.08 (m, 1H) 3.26–3.35(m, 2H), 3.39, 3.43(s×2, 3H), 4.15–4.26(m, 1H), 4.45(br.s, 2H), 4.77–4.86(m, 1H), 6.48, 6.49(s×2, 1H), 8.07(s, 1H), 8.16, 8.22(d×2, J=7 Hz, 1H)

EXAMPLE 9 cis-N-(3-Methoxy-4-piperidinyl)-4-amino-5-chloro-2-((S)-1-methyl-2-butynyl)oxybenzamide hydrochloride

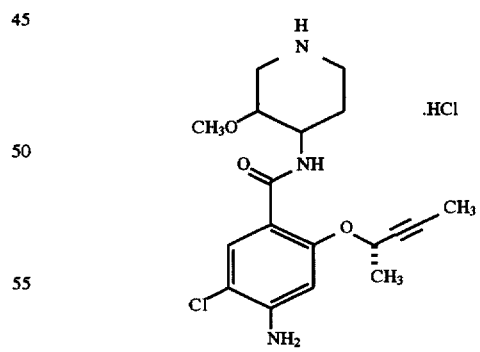

The title compound was prepared in a similar manner to that of the Example 2.

$^1$H-NMR (400 MHz, d$_6$-DMSO) δ ppm:

1.62 (d, J=7 Hz, 3H), 1.67–1.86(m, 2H), 1.81(s, 3H), 2.92–3.16(m, 3H), 3.35, 3.39(s×2, 3H), 3.50–3.64(m, 2H), 4.16–4.26(m, 1H), 5.00–5.08(m, 1H), 6.59, 6.61 (s×2, 1H), 7.71, 7.73(s×2, 1H), 8.06(d, J=7 Hz, 1H), 8.21–8.35(m, 1H), 9.28–9.42(m, 1H)

MS m/z (FAB): 366 (M⁺+1)

EXAMPLE 10 cis-N-[1-[3-(4-Fluorophenoxyl)propyl]-3-methoxy-4-piperidinyl]-4-amino-5-chloro-2-((S)-1-methyl-2-butynyl)oxybenzamide

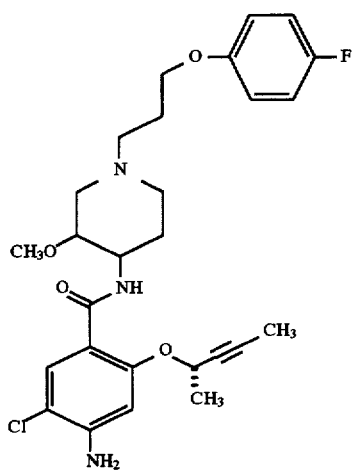

A mixture comprising 0.10 g of the cis-N-(3-methoxy-4-piperidinyl)-4-amino-5-chloro-2-((S)-1-methyl-2-butynyl)oxybenzamide, 0.07 g of 3-(4-fluorophenoxy)propyl bromide, 0.20 g of triethylamine and 10 ml of DMF was stirred at 50° C. for 2 hours and cooled. Ethyl acetate was poured into the resulting mixture. The obtained mixture was washed with water thrice, dried over magnesium sulfate, and freed from the solvent. The residue was purified by silica gel column chromatography (5% methanol/dichloromethane) to give 0.13 g of the title compound.

¹H-NMR (400 MHz, CDCl₃) δ ppm:

1.68, 1.69(d×2, J=7 Hz, 3H), 7.75–2.05(m, 4H), 1.81, 1.82(d×2, J=2 Hz, 3H), 2.07–2.27(m, 2H), 2.47–2.62 (m, 2H), 2.78–2.87(m, 1H), 3.06–3.21(m, 1H), 3.36, 3.42(s×2, 3H), 3.44–3.48(m, 1H), 3.92–3.98(m, 2H), 4.14–4.25(m, 1H), 4.38(br.s, 2H), 4.79–4.86(m, 1H), 6.49, 6.50(s×2, 1H), 6.78–6.85(m, 2H), 6.91–6.98(m, 2H), 8.09, 8.10(s×2, 1H), 8.17, 8.21(d×2, J=7 Hz, 1H)

EXAMPLE 11 cis-N-[1-[3-14-Fluorophenoxy)propyl]-3-methoxy-4-piperidinyl]-4-amino-5-chloro-2-((S)-1-methyl-2-butynyl)oxybenzamide hydrochloride

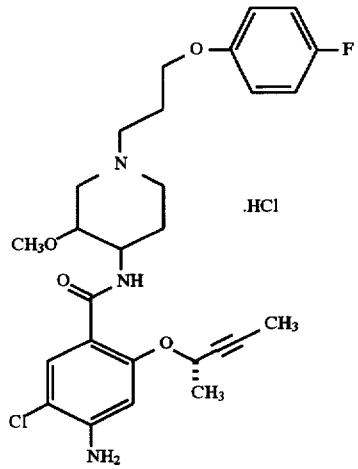

The title compound was prepared in a similar manner to that of the Example 2.

¹H-NMR (400 MHz, d₆-DMSO) δ ppm:

1.62, 1.63(d×2, J=7 Hz, 3H), 1.76–1.98(m, 2H), 1.81, 1.82(d×2, J=2 Hz, 3H), 2.04–2.26(m, 2H), 3.07–3.62 (m, 5H), 3.39, 3.43(s×2, 3H), 3.66–3.73(m, 1H), 3.82–3.89(m, 1H), 3.98–4.04(m, 2H), 4.16–4.26(m, 1H), 4.98–5.05(m, 1H), 6.60, 6.62(s×2, 1H), 6.92–6.98 (m, 2H), 7.10–7.16(m, 2H), 7.73, 7.74(s×2, 1H), 8.06, 8.08(d×2, J=7 Hz, 1H), 9.32–9.48(m, 1H)

MS m/z (FAB): 518 (M⁺+1)

EXAMPLE 12 cis-N-(1-Methyl-3-methoxy-4-piperidinyl)-4-amino-5-chloro-2-((S)-1-methyl-2-butynyl)oxybenzamide

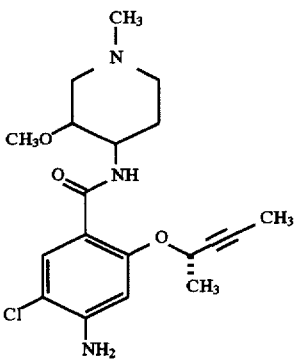

The title compound was prepared in a similar manner to that of the Example 10.

¹H-NMR (400 MHz, CDCl₃) δ ppm:

1.71, 1.72(d×2, J=7 Hz, 3H), 1.75–2.00(m, 2H), 1.82, 1.84(d×2, J=2 Hz, 3H), 2.04–2.17(m, 2H), 2.29, 2.30

(s×2, 3H), 2.78–2.84(m, 1H), 3.01–3.14(m, 1H), 3.39, 3.46(s×2, 3H), 3.40–3.45(m, 1H), 4.10–4.20(m, 1H), 4.36(br.s, 2H), 4.80–4.88(m, 1H), 6.53, 6.57(×2, 1H), 8.15(s, 1H), 8.01, 8.01(d×2, J=7 Hz, 1H)

EXAMPLE 13 cis-N-(1-Methyl-3-methoxy-4-piperidinyl)-4-amino-5-chloro-2-((S)-1-methyl-2-butynyl)oxybenzamide hydrochloride

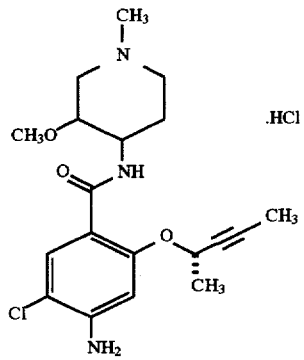

The title compound was prepared in a similar manner to that of the Example 2.

$^1$H-NMR (400 MHz, $d_6$-DMSO) δ ppm:

1.62(d, J=7 Hz, 3H), 1.74–1.92(m, 2H), 1.81(s, 3H), 2.74(s, 3H), 3.03–3.84(m, 5H), 3.37, 3.42(s×2, 3H), 4.11–4.21(m, 1H), 4.98–5.10(m, 1H), 6.08(s, 2H), 6.59 (s, 1H), 7.72(s, 1H), 8.01–8.08(m, 1H), 9.16–9.32(m, 1H)

MS m/z (FAB): 380 (M$^+$+1)

EXAMPLE 14

N-(4-Oxa-1-azabicyclo[3.3.1]non-6α-yl)-4-amino-5-chloro-2-((S)-1-methyl-2-butynyl)oxybenzamide chloro-2-((S)-1-methyl-2-butynyl)oxybenzamide

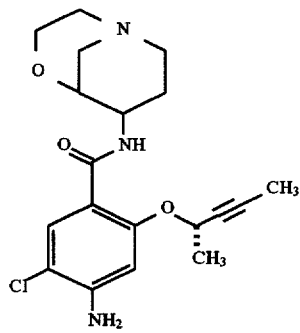

The title compound was prepared in a similar manner to that of the Example 1.

$^1$H-NMR (400 MHz, CDCl$_3$) δ ppm:

1.72(d, J=7 Hz, 3H), 1.83, 1.86(d×2, J=7 Hz, 3H), 1.88–2.05(m, 1H), 2.14–2.24(m, 1H), 2.77–2.84(m, 1H), 2.92–3.02(m, 1H), 3.05–3.20(m, 2H), 3.41–3.49 (m, 2H), 3.69–3.84(m, 2H), 3.95–4.05(m, 1H), 4.19–4.30 (m, 1H), 4.51–4.56 (m, 2H), 4.83–4.91 (m, 1H), 6.52, 6.55(s×2, 1H), 8.06(s, 1H), 8.34–8.42(m, 1H)

EXAMPLE 15

N-(4-Oxa-1-azabicyclo[3.3.1]non-6α-yl)-4-amino-5-chloro-2-((S)-1-methyl-2-butynyl)oxybenzamide hydrochloride

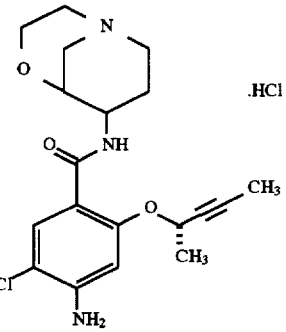

The title compound was prepared in a similar manner to that of the Example 2.

1H-NMR (400 MHz, $d_6$-DMSO) δ ppm:

1.62(d, J=7 Hz, 3H), 1.82(s, 3H), 2.06–2.15(m, 2H), 2.98–3.07(m, 1H), 3.24–4.30(m, 11H), 4.97–5.05(m, 1H), 6.60(s, 1H), 7.72(s, 1H), 8.08–8.15(m, 1H), 11.45 (br.s, 1H)

MS m/z (FAB): 378 (M$^+$+1)

EXAMPLE 16

N-((6S)- or (6R)-6β-hydroxy-8-methyl-8-azabicyclo[3.2.1]oct-3α-yl)-4-amino-5-chloro-2-((S)-1-methyl-2-butynyl)oxybenzamide

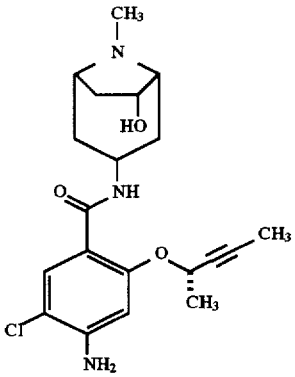

The same procedure as that of the Example 1 was repeated except that 3-amino-6-hydroxy-8-methyl-8-azabicyclo [3.2.1]octane was used as the azabicyclo component. The obtained product was purified by HPLC with a column for the separation of optical isomers (Chiralcel OD, a product of Daicel Chemical Industries, Ltd., 20φ×250 mm) to give the title compounds.

mobile phase: ethanol/n-hexane/triethylamine (10:90:0.5) mixture

The following fraction 1 refers to that of a shorter retention time, while the following fraction 2 refers to that of a longer retention time.

<fraction 1>

$^1$-NMR (400 MHz, CDCl$_3$) δ ppm:

1.45–1.52(m, 1H), 1.65–1.74(m, 1H), 1.71(d, J=7 Hz, 3H), 1.84(d, J=2 Hz, 3H), 1.97–2.05(m, 1H), 2.23–2.34 (m, 2H), 2.47–2.54(m, 1H), 2.56(s, 3H), 3.03–3.07(m, 1H), 3.30–3.35(m, 1H), 4.19(q, J=7 Hz, 1H), 4.39(br.s, 2H), 4.53(dd, J=3 Hz, 7 Hz, 1H), 4.91–4.98(m, 1H), 6.44(s, 1H), 7.86(d, J=6 Hz, 1H), 8.05(s, 1H)

MS m/z (FAB): 392 (M$^+$+1)

<fraction 2>

$^1$H-NMR (400 MHz, CDCl$_3$) δ ppm:

1.42–1.49(m, 1H), 1.67–1.74(m, 1H), 1.71(d, J=7 Hz, 3H), 1.86(d, J=2 Hz, 3H), 1.97–2.05(m, 1H), 2.22–2.34 (m, 2H), 2.48–2.56(m, 1H), 2.56(s, 3H), 3.03–3.06(m, 1H), 3.30–3.34(m, 1H), 4.19(q, J=7 Hz, 1H), 4.39(br.s, 2H), 4.54(dd, J=3 Hz, 7 Hz, 1H), 4.90–4.97(m, 1H), 6.46(s, 1H), 7.88(d, J=6 Hz, 1H), 8.06(s, 1H)

MS m/z (FAB): 392 (M$^+$+1)

EXAMPLE 17

N-(DL-6α-Hydroxy-8-methyl-8-azabicyclo[3.2.1]oct-3α-yl)-4-amino-5-chloro-2-((S)-1-methyl-2-butynyl)oxybenzamide

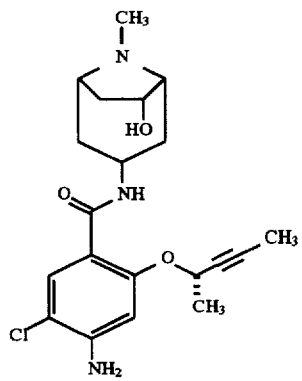

The title compound was obtained as another fraction in a small amount in the HPLC of the Example 16.

$^1$H-NMR (400 MHz, CDCl$_3$) δ ppm:

1.20–2.10(m, 4H), 1.66(d, J=7 Hz, 3H), 1.87(d, J=2 Hz, 3H), 2.29–2.38(m, 2H), 2.48(s, 8H), 3.10–3.15(m, 1H), 3.24–3.30(m, 1H), 4.24–4.34(m, 3H), 4.72–4.78(m, 1H), 4.80–4.87(m, 1H), 6.43(s, 1H), 7.95(s, 1H), 8.85 (d, J=7 Hz, 1H)

EXAMPLE 18

(S)-N-(3,9-Dimethyl-3,9-diazabicyclo[3.3.1]non-7α-yl)-4-amino-5-chloro-2-(1-methyl-2-butynyl)oxybenzamide

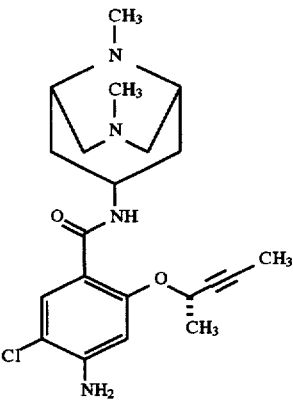

The title compound was prepared in a similar manner to that of the Example 1.

$^1$H-NMR (400 MHz, CDCl$_3$) δ ppm:

1.43–1.50(m, 2H), 1.58(d, J=7 Hz, 3H), 1.83(d, J=2 Hz, 3H), 2.23(s, 3H), 2.38–2.56(m, 4H), 2.51(s, 3H), 2.56–2.62(m, 1H), 2.68–2.74(m, 1H), 2.80–2.88(m, 1H), 4.25(s, 2H), 4.50(q, J=6 Hz) 1 Hz), 4.65–4.72(m, 1H), 6.53(s, 1H), 7.68(s, 1H) 9.93(3, J=6 Hz), 1H)

EXAMPLE 19

(S)-N-(3,9-Dimethyl-3,9-diazabicyclo[3.3.1]non-7α-yl)-4-amino-5-chloro-2-(1-methyl-2-butynyl)oxybenzamide dihydrochloride

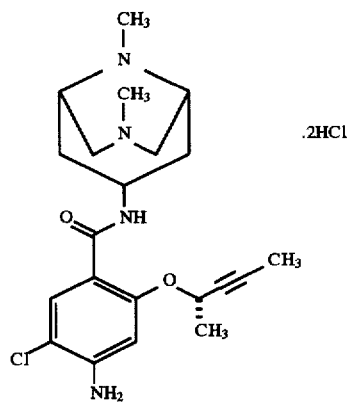

The title compound was prepared in a similar manner to that of the Example 2.

MS m/z (FAB): 405 (M$^+$+1)

EXAMPLE 20

N-((5S)- or (5R)-4-Oxa-1-azabicyclo[3.3.1]non-6α-yl)-4-amino-5-chloro-2-((S)-1-methyl-2-butynyl) oxybenzamide hydrochloride

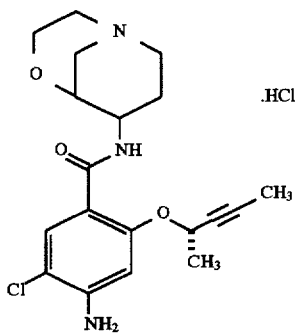

The product of the Example 14 was separated by HPLC with a column for the separation of optical isomers (Chiralcel OD, a product of Daicel Chemical inductries, Ltd., 20φ×250 mm) to give the title compounds.

mobile phase: ethanol/n-hexane/triethylamine (20:80:0.5) mixture

The following fraction 1 refers to that of a shorter retention time, while the following fraction 2 refers to that of a longer retention time.

The isomers thus prepared were each converted into their respective hydrochlorides according to the process of the Example 2.

<hydrochloride of fraction 1>

$^1$-NMR (400 MHz, d$_6$-DMSO) δ ppm:

1.61(3, J=7 Hz, 3H), 1.81(d, J=2 Hz, 3H), 2.02–2.18(m, 2H), 3.26–3.46(m, 4H), 3.49–3.58(m, 1H), 3.67–3.75 (m, 1H), 3.91–4.04(m, 2H), 4.08–4.12(m, 1H), 4.17–4.25(m, 1H), 4.96–5.08(m, 1H), 6.08(br.s, 2H), 6.59(2, 1H), 7.72(s, 1H), 8.12(d, J=7 Hz, 1H), 10.57 (br.s, 1H)
MS m/z (FAB): 378 (M$^+$+1)
$[\alpha]_D^{23}$ =−63.46° (C=1, MeOH)

<hydrochloride of fraction 2>

$^1$H-NMR (400 MHz, d$_6$-DMSO) δ ppm:

1.61(d, J=7 Hz, 3H), 1.82(d, J=2 Hz, 3H), 2.08–2.17(m, 2H), 3.26–3.44(m, 4H), 3.47–3.56(m, 1H), 3.67–3.74 (m, 1H), 3.90–4.03(m, 2H), 4.04–4.08(m, 1H), 4.16–4.25(m, 1H), 4.97–5.05(m, 1H), 6.59(s, 1H), 7.71 (s, 1H), 8.11(d, J=7 Hz, 1H), 1.07(br.s, 1H)
MS m/z (FAB): 378 (M$^+$+1)
$[\alpha]_D^{23}$=−169.90° (C=1, MeOH)

EXAMPLE 21

N-(4-Oxa-1-azabicyclo[3.3.1]non-6β-yl)-4-amino-5-chloro-2-((S)-1-methyl-2-butynyl)oxybenzamide

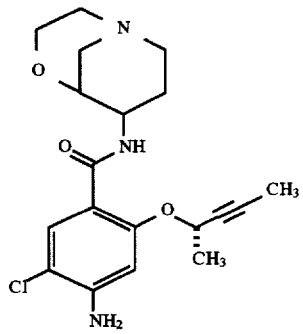

The title compound was prepared as a minor product in the mass-production of the Example 20.

$^1$H-NMR (400 MHz, CDCl$_3$) δ ppm:

1.53–1.64(m, 1H), 1.70(d, J=7 Hz, 3H), 1.85(d, J=2 Hz, 3H), 2.54–2.66(m, 1H), 2.94–3.05(m, 2H), 3.19–3.30 (m, 1H), 3.37–3.60(m, 2H), 3.68–3.80(m, 2H), 4.02–4.10(m, 1H), 4.40–4.53(m, 2H), 4.78–4.92(m, 1H), 6.48(s, 1H), 8.02(d, J=6 Hz, 1H), 8.10(s, 1H)

EXAMPLE 22

N-(4-Oxa-1-azabicyclo[3.3.1]non-6β-yl)-4-amino-5-chloro-2-((S)-1-methyl-2-butynyl)oxybenzamide hydrochloride

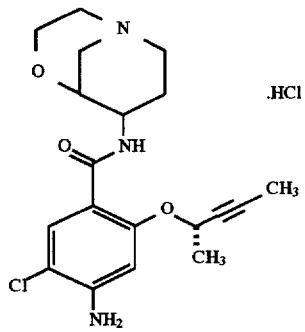

The title compound was prepared in a similar manner to that of the Example 2.

$^1$H-NMR (400 MHz, d$_6$-DMSO) δ ppm:

1.59(d, J=7 Hz, 3H), 1.74–1.85(m, 1H), 1.82(d, J=2 Hz, 3H), 2.56–2.71(m, 1H), 3.18–3.78(m, 4H), 3.84–4.12 (m, 6H), 4.88–5.06(m, 1H), 5.96, 6.10(br.s×2, 2H), 6.58, 6.59(s×2, 1H), 7.48, 7.49(×2, 1H), 7.91, 7.95(d× 2, J=7 Hz, 1H), 10.90(br.s, 1H)
MS m/z (FAB): 378 (M$^+$+1)

EXAMPLE 23

N-((6R)- or (6S)-6β-Methoxy-8-methyl-8-azabicyclo-[3.2.1]oct-3β-yl)-4-amino-5-chloro-2-((S)-1-methyl-2-butynyl)oxybenzamide

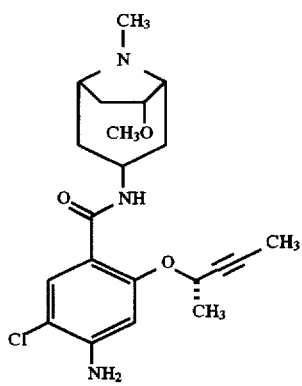

The same procedure as that of the Example 1 was repeated except that 3-amino-6-methoxy-8-methyl-8-azabicyclo[3.2.1]octane was used as the azabicyclo component. The obtained product was separated by HPLC with a column for the separation of optical isomers (Chiralcel OJ, a product of Daicel Chemical Industries, Ltd., mobile phase: ethanol/n-hexane/triethylamine (10:90:0.5) mixture). The first fraction was further separated by HPLC with chiralcel OD (a product of Daicel Chemical Industries, Ltd., mobile phase: ethanol/n-hexane/triethylamine (10:90:0.5) mixture) to give the title compounds.

The obtained fractions were numbered 1, 2 and 3 in the order of increasing retention time.

<fraction 1>

1H-NMR (405 MHz, CDCl$_3$) δ ppm:

1.54–1.66(m, 2H), 1.66(d, J=7 Hz, 3H), 1.77–1.82(m, 1H), 1.83(d, J=2 Hz, 3H), 1.87–1.95(m, 1H), 2.05–2.19 (m, 2H), 2.51(s, 3H), 3.23–3.26(m, 1H), 8.29(s, 3H), 3.36–3.41(m, 1H), 8.92–3.96(m, 1H), 3.99–4.12(m, 1H), 4.38(br.s, 2H), 4.78–4.85(m, 1H), 8.48(s, 1H), 7.82(d, J=6 Hz, 1H), 8.02(s, 1H)

<fraction 3>

$^1$H-NMR (400 MHz, CDCl$_3$) δ ppm:

1.55–1.64(m, 2H), 1.67(d, J=7 Hz, 3H), 1.75–1.81(m, 1H), 1.83(d, J=2 Hz, 8H), 1.91–2.19(m, 3H), 2.51(s, 3H), 3.23–3.27(m, 1H), 3.29(s, 3H), 3.35–3.40(m, 1H), 3.93–3.97(m, 1H), 3.98–4.14(m, 1H), 4.36(br.s, 2H) 4.78–4.85(m, 1H), 6.45(s, 1H), 7.61(d, J=6 Hz, 1H), 8.03(s, 1H)

EXAMPLE 24

N-((6S)- or (6R)-6β-Methoxy-8-methyl-8-azabicyclo-[3.2.1]oct-3β-yl)-4-amino-5-chloro-2-((S)-1-methyl-2-butynyl)oxybenzamide hydrochloride

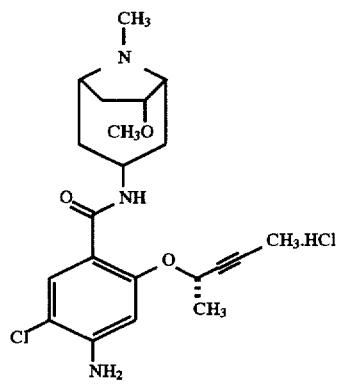

The fractions 1 and 3 of the Example 23 were each treated according to the process of the Example 2 to give the title compounds.

<hydrochloride of fraction 1 of Example 23>

$^1$H-NMR (400 MHz, d$_6$-DMSO) δ ppm:

1.64(d, J=7 Hz, 3H), 1.82(d, J=2 Hz, 3H), 1.95–2.27(m, 5H), 2.42–2.50(m, 1H), 2.75(d, J=6Hz, 3H), 3.26(s, 3H), 3.97–4.11(m, 4H), 4.95–5.02(m, 1H), 6.58(s, 1H), 7.64(s, 1H), 7.65(d, J=7 Hz, 1H), 10.92(m, 1H)

MS m/z (FAB): 406 (M$^+$+1)

<hydrochloride of fraction 3 of Example 23>

1H-NMR (400 MHz, d$_6$-DMSO) δ ppm:

1.64(d, J=7 Hz, 3H), 1.82(d, J=2 Hz, 3H), 1.92–2.08 (m, 3H), 2.10–2.17(m, 1H), 2.20–2.28(m, 1H), 2.42–2.49 (m, 1H), 2.76(d, J=6 Hz, 3H), 3.26(s, 3H), 3.95–4.12 (m, 4H), 4.95–5.03(m, 1H), 6.05(br.s, 2H), 6.58(s, 1H), 7.64(s, 1H), 7.65(d, J=7 Hz, 1H), 10.75(m, 1H)

MS m/z (FAB): 406 (M$^+$+1)

EXAMPLE 25

N-(6α-Methoxy-8-methyl-8-azabicyclo[3.2.1]oct-3α-yl)-4-amino-5-chloro-2-((S)-1-methyl-2-butynyl)oxybenzamide

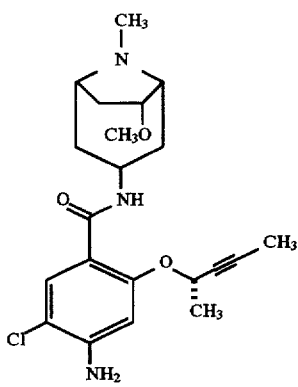

The title compound was obtained as the fraction 2 in the HPLC of the Example 23.

$^1$H-NMR (400 MHz, CDCl$_3$) δ ppm:

1.64, 1.67(d×2, J=7 Hz, 3H), 1.80, 1.86(d×2, J=2 Hz, 3H), 1.68–2.00(m, 4H), 2.21–2.42(m, 3H), 2.43, 2.44(s×2, 3H), 3.05–3.10(m, 1H), 3.22–3.26(m, 1H), 3.33, 3.45 (s×2, 3H), 4.13–4.20(m, 1H), 4.27, 4.30(br.s×2, 2H), 4.67, 4.78(m×2, 1H), 6.45, 6.60(s×2, 1H), 7.81, 7.83 (s×2, 1H), 8.41, 8.44(d×2, J=6 Hz, 1H)

EXAMPLE 26

N-(6α-Methoxy-8-methyl-8-azabicyclo[3.2.1]oct-3α-yl)-4-amino-5-chloro-2-((S)-1-methyl-2-butynyl)oxybenzamide hydrochloride

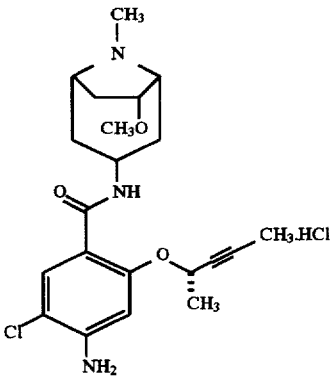

The title compound was prepared in a similar manner to that of the Example 2.

$^1$H-NMR (400 MHz, d$_6$-DMSO) δ ppm:

1.55, 1.58(d×2, J=7 Hz, 3H), 1.77, 1.84(d×2, J=2 Hz, 3H), 1.80–2.11(m, 3H), 2.42–2.53(m, 1H), 2.56–2.70(m, 4H), 2.76–2.79(m, 1H), 3.31, 3.42 (s×2, 3H), 3.61–4.48 (m, 4H), 4.82–5.00(m, 1H), 6.55, 6.62(s×2, 1H), 7.50, 7.52(s×2, 1H), 8.07–8.18(m, 1H), 10.55, 10.90(m×2, 1H)

MS m/z (FAB): 406 (M$^+$+1)

EXAMPLE 27

N-((6S)- or (6R)-6β-Methoxy-8-methyl-8-azabicyclo[3.2.1]-oct-3α-yl)-4-amino-5-chloro-2-((S)-1-methyl-2-butynyl)oxybenzamide

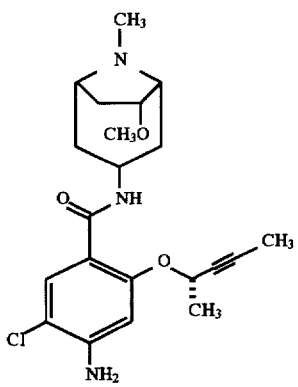

The second fraction obtained by the HPLC with a column for the separation of optical isomers (Chiralcel OJ) in the Example 23 was further separated with Chiralcel OD under the same conditions as those of the Example 23 to give the title compounds.

The obtained fractions were numbered 1 and 2 in the order of increasing retention time.

<fraction 1>

$^1$-NMR (400 MHz; CDCl$_3$) δ ppm:

1.70(d; J=7 Hz, 3H), 1.84(d, J=2 Hz, 3H), 2.06–2.16(m, 2H), 2.21–2.39(m, 4H), 2.51(s, 3H), 3.16–3.20(m, 1H), 3.26(s, 3H), 3.28–3.34(m, 1H), 4.08–4.13(m, 1H), 4.17 (q, J=7 Hz, 1H), 4.40(br.s, 2H), 4.90–4.98(m, 1H), 6.47(s, 1H), 7.87(d, J=6 Hz, 1H), 8.08(s, 1H)

<fraction 2>

$^1$H-NMR (400 MHz, CDCl$_3$) δ ppm:

1.71(d, J=7 Hz, 3H), 1.83(d, J=2 Hz, 3H), 2.05–2.12(m, 1H), 2.12–2.37(m, 3H), 2.51(s, 3H), 3.17–3.21(m, 1H), 3.26–3.34(m, 1H), 3.28(s, 3H), 4.08–4.13(m, 1H), 4.16 (q, J=7 Hz, 1H), 4.40(br.s, 2H), 4.92–4.98(m, 1H), 6.44(s, 1H), 7.88(d, J=6 Hz, 1H), 8.08(s, 1H)

EXAMPLE 28

N-((6S)- or (6R)-6β-Methoxy-8-methyl-8-azabiscyclo[3.2.1]oct-3α-yl) -4-amino-5-chloro-2-((S)-1-methyl-2-butynyl)oxybenzamide hydrochloride

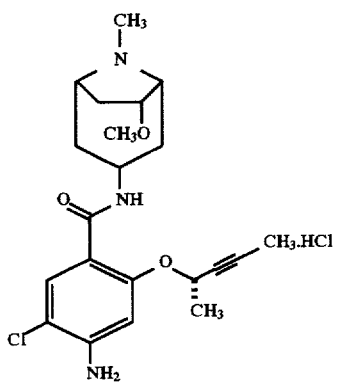

The fractions 1 and 2 obtained in the Example 27 were each treated in a similar manner to that of the Example 2 to give the title compounds.

<hydrochloride of fraction 1 of Example 27>

$^1$H-NMR (400 MHz, d$_6$-DMSO) δ ppm:

1.62(d, J=7 Hz, 3H), 1.81(d, J=2 Hz, 3H), 1.84–2.34(m, 3H), 2.41–2.78(m, 5H), 3.08–3.45(m, 1H), 3.24(s, 3H), 3.58–3.76(m, 1H), 3.84–4.00(m, 2H), 4.10–4.26(m, 1H), 5.05–5.13(m, 1H), 6.00(br.s, 2H), 6.61(s, 1H), 7.60(s, 1H), 7.79(d, J=7 Hz, 1H)

MS m/z (FAB): 406 (M$^+$+1)

<hydrochloride of fraction 2 of Example 27>

$^1$H-NMR (400 MHz, d$_6$-DMSO) δ ppm:

1.62(d, J=7 Hz, 3H), 1.82(d, J=2 Hz, 3H), 1.98–2.05 (m, 1H), 2.10–2.17(m, 1H), 2.24–2.32(m, 1H), 2.46–2.56 (m, 1H), 2.61–2.69(m, 1H), 2.78(d, J=6 Hz, 3H), 3.25(s, 3H), 3.32–3.54(m, 1H), 3.90–3.97(m, 1H), 3.99–4.06(m, 2H), 4.22–4.27(m, 1H), 5.05–5.13(m, 1H), 6.00(br.s, 2H), 6.60(s, 1H), 7.59(s, 1H), 7.78(d, J=7 Hz, 1H), 10.58(br.s, 1H)

MS m/z (FAB): 406 (M$^+$+1)

EXAMPLE 29

N-(8-Azabicyclo[3.2.1]oct-3α-yl)-4-amino-5-chloro-2-((S)-1-methyl-2-butynyl)oxybenzamide

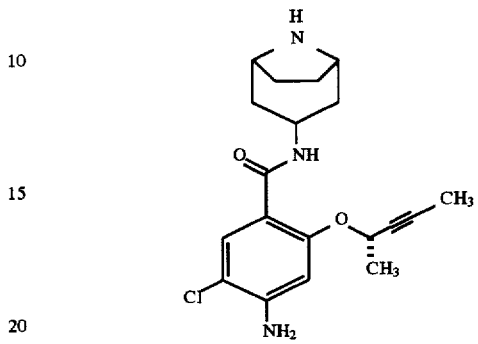

0.75 g of (S)-N-(8-methyl-8-azabicyclo[3.2.1]oct-3α-yl) -4-amino-5-chloro-2-(1-methyl-2-butynyl)oxybenzamide, 0.51 g of 2,2,2-trichloroethyl chlorocarbonate and 0.41 g of potassium carbonate were added to toluene. The obtained mixture was refluxed for 3 hours and cooled, followed by the addition thereto of dichloromethane. The resulting mixture was washed with 1N hydrochloric acid, dried over magnesium sulfate, and freed from the solvent. The residue was purified by silica gel column chromatography (ethyl acetate/n-hexane (1:4) mixture) to give 0.50 g of (S)-N-(S-(2,2,2-trichloroethoxycarbonyl)-8-azabicyclo-[3.2.1]oct-3α-yl)-5-chloro-2-(1-methyl-2-butynyl) oxy-4-(2,2,2-trichloroethoxycarbonylamino)benzamide.

$^1$H-NMR (400 MHz, CDCl$_3$) δ ppm:

1.71(d, J=7 Hz, 3H), 1.83(d, J=2 Hz, 3H), 1.84–1.97(m, 2H), 2.00–2.16(m, 4H), 2.28–2.38(m, 2H), 4.33(q, J=7 Hz, 1H), 4.36–4.44(m, 2H), 4.65–4.93(m, 2H), 4.86(d, J=2 Hz, 2H), 5.10–5.18(m, 1H), 7.53(s, 1H), 8.17(br.s, 1H), 8.22(s, 1H), 8.24(br.s, 1H)

This compound was stirred in 90% acetic acid in the presence of powdered zinc at room temperature overnight and filtered. The filtrate was freed from the solvent, followed by the addition thereto of 1N sodium hydroxide. The resulting mixture was extracted with chloroform thrice and the combined organic phases were dried over magnesium sulfate, and freed from the solvent. The residue was purified by thin-layer chromatography (15% methanol/chloroform) to give 30 mg of the title compound.

$^1$-NMR (400 MHz, CDCl$_3$) δ ppm:

1.68(d, J=6.5 Hz, 3H), 1.83(d, J=2 Hz, 3H), 1.85–1.95(m, 2H), 1.98–2.09(m, 4H), 2.23–2.33(m, 2H), 3.62–3.77 (m, 2H); 4.28(q, J=6 Hz, 1H), 4.38(br.s, 2H), 4.90–4.98 (m, 1H), 6.43(s, 1H), 8.02(d, J=6 Hz, 1H), 8.08(s, 1H)

MS m/z (FAB): 362 (M$^+$+1)

EXAMPLE 30

N-((5S)- or (5R)-1-Azabicyclo[3.3.1]non-4α-yl)-4-amino-5-chloro-2-((S)-1-methyl-2-butynyl)oxybenzamide

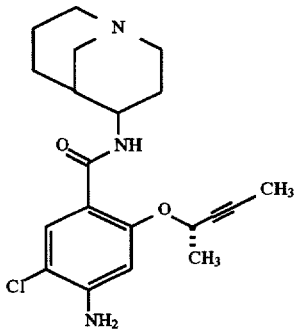

The product of the Example 5 was, separated by HPLC with a column for the separation of optical isomers (Chiralcel OD, a product of Daicel Chemical Industries, Ltd., mobile phase: ethanol/n-hexane/triethylamine (85:15:0.5) mixture) to give the title compounds.

The following fraction 1 refers to that of a shorter retention time, while the following fraction 2 refers to that of a longer retention time.

<fraction 1>

$^1$H-NMR (400 MHz, CDCl$_3$) δ ppm:

1.40–2.01(m, 7H), 1.68(d, J=7 Hz, 3H), 1.84(d, J=4 Hz, 8H), 2.90–3.22(m, 6H), 4.40(br.s, 2H), 4.33–4.54(m, 1H), 4.85–4.98(m, 1H), 6.48(s, 1H), 7.84(d, J=8 Hz, 1H), 8.50(s, 1H)

<fraction 2>

$^1$H-NMR (400 MHz, CDCl$_3$) δ ppm:

1.39–2.07(m, 7H), 1.67(d, J=7 Hz, 3H), 1.84(d, J=4 Hz, 3H), 2.90–3.22(m, 6H), 4.39(br.s, 2H), 4.33–4.52(m, 1H), 4.85–4.93(m, 1H), 6.50(s, 1H), 7.84(d, J=8 Hz, 1H), 8.50(s, 1H)

EXAMPLE 31

N-((5S)- or (5R)-1-Azabicyclo[3.3.1]-non-4α-yl)-4-amino-5-chloro-2-((S)-1-methyl-2-butynyl)oxybenzamide hydrochloride

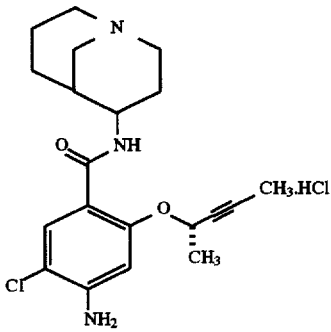

The fractions 1 and 2 obtained in the Example 30 were each treated in a similar manner to that of the Example 2 to give the title compounds.

<hydrochloride of fraction 1 of Example 30>

$^1$H-NMR (400 MHz, d$_6$-DMSO) δ ppm:

1.59(d, J=7 Hz, 3H), 1.62–2.22(m, 7H), 1.83(d, J=4 Hz, 3H), 3.19–3.42(m, 6H), 4.30–4.40(m, 1H), 4.97–5.06 (m, 1H), 6.60(s, 1H), 7.60(s, 1H), 7.82(d, J=8 Hz, 1H), 10.70(br.s, 1H)

MS m/z (FAB): 376 (M$^+$+1)

$[α]_D^{23}$=−112.38° (C=0.2, MeOH)

<hydrochloride of fraction 2 of Example 30>

$^1$H-NMR (400 MHz, d$_6$-DMSO) δ ppm:

1.58(d, J=7 Hz, 3H), 1.62–2.23(m, 7H), 1.81(d, J=4 Hz, 3H), 3.16–3.40(m, 6H), 4.30–4.39(m, 1H), 4.97–5.06 (m, 1H), 6.60(s, 1H), 7.60(s, 1H), 7.82(d, J=8 Hz, 1H), 10.65(br.s, 1H)

MS m/z (FAB): 376 (M$^+$+1)

$[α]_D^{\leq}$=−80.86° (C=1, MeOH)

EXAMPLE 32

N-(1-Azabicyclo[3.3.1]non-4β-yl)-4-amino-5-chloro-2-((S)-1-methyl-2-butynyl)oxybenzamide

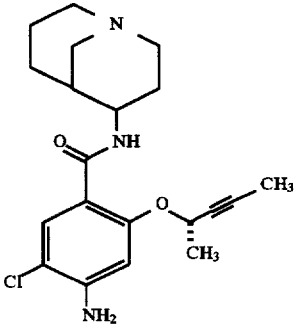

The title compound was obtained as another fraction in the HPLC of the Example 30.

$^1$H-NMR (400 Hz, CDCl$_3$) δ ppm:

1.47–2.42(m, 7H), 1.70, 1.72(d×2, J=9 Hz, 3H), 1.84, 1.85(d×2, J=4 Hz, 3H), 2.81–2.88(m, 1H), 2.98–3.33 (m, 5H), 4.32–4.45(m, 1H), 4.37(br.s, 2H), 4.86–4.93 (m, 1H), 6.47(s, 1H), 8.48(s, 1H), 8.18(d, J=9 Hz, 1H)

EXAMPLE 33

N-(1-Azabicyclo[3.2.1]non-4β-yl)-4-amino-5-chloro-2-((S)-1-methyl-2-butynyl)oxybenzamide hydrochloride

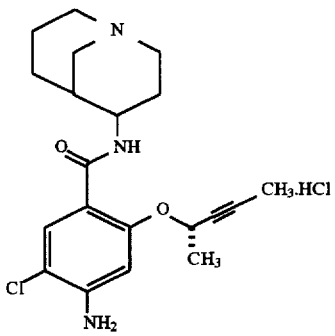

The title compound was prepared in a similar manner to that of the Example 2.

$^1$H-NMR (400 MHz, d$_6$-DMSO) δ ppm:

1.58(d, J=8Hz, 3H), 1.62–1.92(m, 4H), 1.82(d, J=4 Hz, 3H), 2.06–2.20(m, 2H), 2.38–2.50(m, 1H), 3.00–3.40 (m, 6H), 4.02–4.08(m, 1H), 4.92–4.98(m, 1H), 6.59(s, 1H), 7.52(s, 1H), 7.86–8.02(br.s, 1H), 10.74(br.s, 1H)

MS m/z (FAB): 376 (M$^+$+1)

EXAMPLE 34

(S)-N-(3-Methyl-3-azabicyclo[3.2.1]oct-8α- or 8β-yl)-4-amino-5-chloro-2-(1-methyl-2-butynyl)oxybenzamide

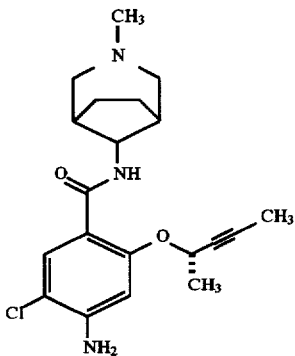

700 mg of (S)-4-amino-5-chloro-2-[(1-methyl-2-butynyl)oxy]benzoic acid and 740 mg of 8-amino-3-methyl-3-azabicyclo[3.2.1]octane were dissolved in 25 ml of pyridine. 370 mg of 1-ethyl-3-(3-dimethyl-aminopropyl)carbodiimide hydrochloride (hereinafter abbreviated to "WSC.HCl") and 590 mg of 1-hydroxy-benzotriazole (HOBT) were added to the obtained solution under stirring at room temperature. The obtained mixture was stirred overnight and distilled in a vacuum to remove the solvent. The residue was extracted with a 2N aqueous solution of sodium hydroxide and chloroform. The organic phase was dried over anhydrous magnesium sulfate and concentrated in a vacuum. The residue was purified by silica gel column chromatography (1 to 10 to 20% methanol/chloroform) to give two products. The first eluate was composed of the 8α isomer (264 mg), while the second eluate was composed of the 8β isomer (13 mg).

<8α isomer>

$^1$H-NMR (400 MHz, CDCl$_3$) δ ppm:

8.15(s, 1H), 8.08(d, J=6 Hz, 1H), 6.05(s, 1H), 4.95(dd, J=6.4 Hz, 2.0 Hz, 1H), 4.37(br.s, 2H), 4.04–4.09(dd, J=6.6 Hz, 5.2 Hz, 1H), 2.56–2.62(br.d, J=11.0 Hz, 2H), 2.82–2.44(m, 2H), 2.30(s, 8H), 2.25(br.s, 2H), 2.37–1.76(m+d, J=2.0 Hz, 7H), 1.74(d, J=6.4 Hz, 3H)

<8β isomer>

$^1$H-NMR (400 MHz, CDCl$_3$) δ ppm:

8.10(s, 1H), 7.69(d, J=6.8 Hz, 1H), 6.46(s, 1H), 4.85–4.92 (dd, J=6.6 Hz, 2.0 Hz, 1H), 4.37–4.40(br.s, 2H), 4.02–4.06(d, J=7.0 Hz, 1H), 2.83–2.86(br.d, J=7.8 Hz, 2H), 2.24–2.42(m+s, 7H), 1.80–1.94(m+d, J=2 Hz, 7H), 1.67(d, J=6.4 Hz, 3H)

EXAMPLE 35

(S)-N-(3-Methyl-2-azabicyclo[3.2.1]oct-8α-yl)-4-amino-5-chloro-2-(1-methyl-2-butynyl) oxybenzamide hydrochloride

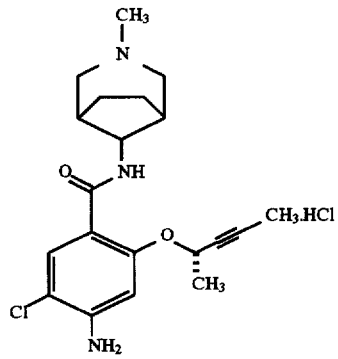

264 mg of (S)-N-(3-methyl-3-azabicyclo[3.2.1]oct-8α-yl)-4-amino-5-chloro-2-(1-methyl-2-butynyl)oxybenzamide was dissolved in ethanol, followed by the addition thereto of 140 μl of a 20% ethanolic solution of hydrochloric acid at room temperature. The obtained solution was concentrated in a vacuum, followed by the addition thereto of diethyl ether. The salt thus precipitated was recovered by filtration. 228 mg of the title compound was obtained.

$^1$H-NMR (400 MHz, d$_6$-DMSO) δ ppm:

10.10(br.s, 1H), 7.99(d, J=5.1 Hz, 1H), 7.55(s, 1H), 6.62(s, 1H), 5.01(br.d, J=2.0 Hz, 1H), 3.60–3.80(m, 3H), 3.15–3.25(t, J=12.0 Hz, 2H), 3.08–2.99 (t, J=12.0 Hz, 2H), 2.66(d, J=4.6 Hz, 3H), 2.41(br.s, 2H), 1.95–2.02(d, J=9.3 Hz, 2H), 1.78–1.87(m, 5H), 1.59(d, J=6.4 Hz, 3H)

MS m/z (FAB): 376 (M$^+$+1)

EXAMPLE 36

(S)-N-(3-Methyl-3-azabicyclo[3.2.1]oct-8β-yl)-4-amino-5-chloro-2-(1-methyl-2-butynyl) oxybenzamide hydrochloride

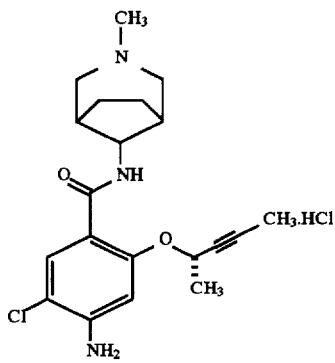

The title compound was prepared in a similar manner to that of the Example 35.

$^1$H-NMR (400 MHz, $d_6$-DMSO) δ ppm:
9.51(br.s, 1H), 7.65(s, 1H), 7.58(d, J=6.4 Hz), 6.58(s, 1H), 4.98–5.05(dd, J=6.4 Hz, 2.0 Hz, 1H), 4.13–4.17(br.d, J=6.7 Hz, 1H), 3.53–3.80(br.s, 2H), 3.26–3.32(m, 2H), 3.15–3.23(m, 2H), 2.65–2.70(d,m J=4.6 Hz, 3H), 2.33–2.38(br.s, 2H), 1.78–1.98(m, 7H), 1.58(d, J=6.4 Hz, 3H)

MS m/z (FAB): 376 (M$^+$+1)

EXAMPLE 37

(S)-N-(3-Isopropyl-3-azabicyclo[3.2.1]oct-8-yl)-4-amino-5-chloro-2-(1-methyl-2-butynyl) oxybenzamide

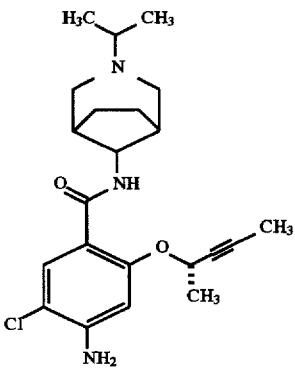

600 mg of (S)-4-amino-5-chloro-2-{(1-methyl-2-butynyl) oxy benzoic acid and 1.03 g of 8-amino-3-isopropyl-3-azabicyclo[3.2.1]octane were dissolved in 6 ml of pyridine. 1.26 g of dicyclohexylcarbodiimide (DCC) was added to the obtained solution under stirring at room temperature. The resulting mixture was stirred overnight, followed by the addition thereto of 6 ml of water. Insolubles were filtered out and the filtrate was basified with an aqueous solution of sodium hydroxide and extracted with chloroform. The organic phase was dried over anhydrous magnesium sulfate and freed from the solvent by distillation. The residue was purified by silicagel column chromatography (5% methanol/chloroform) and then by preparative thin-layer chromatography to give 40 mg of the title compound.

$^1$H-NMR (400 MHz, CDCl$_3$) δ ppm:
8.14(s, 1H), 8.04(d, J=6.0 Hz, 1H), 6.47(s, 1H), 4.92(m, 1H), 4.36(br.s, 2H), 4.00(m, 1H), 2.40–2.69(m, 5H), 2.20–2.55(m, 2H), 1.82(s, 3H), 1.68–1.78(m, 7H), 1.02 (d, J=6.4 Hz, 6H)

EXAMPLE 38

(S)-N-(3-Isopropyl-3-azabicyclo[3.2.1]oct-8-yl)-4-amino-5-chloro-2-(1-methyl-2-butynyl) oxybenzamide hydrochloride

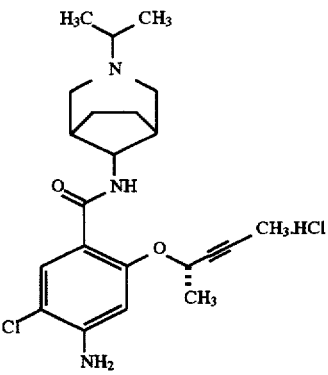

The title compound was prepared in a similar manner to that of the Example 35.

$^1$H-NMR (400 MHz, $d_6$-DMSO) δ ppm:
9.10(br.s, 1H), 7.98(d, J=4.6 Hz), 7.59(s, 1H), 6.60(s, 1H), 6.00(br.s, 2H), 5.03(m, 1H), 3.67(m, 1H), 3.45–2.95(m, 7H), 2.54–2.50(m, 2H), 1.96–2.75(m, 5H), 1.57(d, J=6.0 Hz, 3H), 1.26(d, J=6.4 Hz, 6H)

MS m/z (FAB): 404 (M$^+$+1)

EXAMPLE 39

(S)-N-(3-Benzyl-3-azabicyclo[3.2.1]oct-8-yl)-4-amino-5-chloro-2-(1-methyl-2-butynyl) oxybenzamide

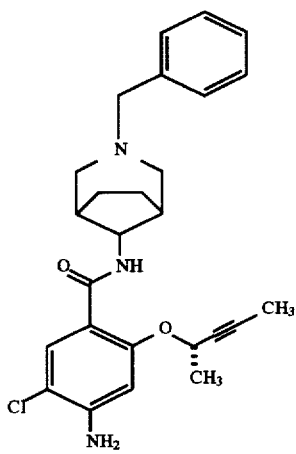

The condensation of 530 mg of (S)-4-amino-5-chloro-2-[(1-methyl-2-butynyl)oxy]benzoic acid with 850 mg of 8-amino-3-benzylazabicyclo[3.2.1]octane was conducted in a similar manner to that of the Example 34 by the use of WSC.HCl and 1-hydroxybenzotriazole (HOBT). The product was purified by silica gel column chromatography (5% methanol/chloroform) to give 220 mg of the title compound.

¹H-NMR (400 MHz, CDCl₃) δ ppm:

8.14(s, 1H), 8.07(d, J=6.6 Hz, 1H), 7.36–7.21(m, 5H), 6.52(s, 1H), 4.97(m, 1H), 4.39(s, 2H), 4.10(m, 1H), 3.53(s, 2H), 2.61–2.55(m, 2H), 2.48–2.40 (m, 2H), 2.21(br.s, 2H), 2.90–2.64(m, 10H)

MS m/z (FAB): 452 (M⁺+1)

EXAMPLE 40

(S)-N-(3-Benzyl-3-azabicyclo[3.2.1]oct-8-yl)-4-amino-5-chloro-2-(1-methyl-2-butynyl)oxybenzamide hydrochloride

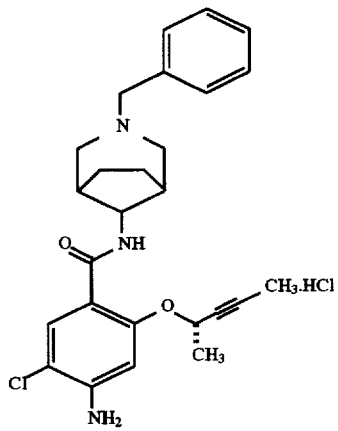

The title compound was prepared in a similar manner to that of the Example 35.

¹H-NMR (400 MHz, d₆-DMSO) δ ppm:

7.89(d, J=4.2 Hz, 1H), 7.66–7.62(m, 2H), 7.49(s, 1H), 7.40–7.35(m, 3H), 6.60(s, 1H), 5.97(br.s, 2H), 4.95(m, 1H), 4.23(br.s, 2H), 3.65(m, 1H), 3.30–3.18(m, 2H), 3.17–2.97(m, 4H), 2.10–1.96(m, 2H), 1.90–1.66(m, 5H), 1.57(d, J=6.4 Hz, 3H)

MS m/z (FAB): 452 (M⁺+1)

EXAMPLE 41

N-(8-Methyl-8-azabicyclo[3.2.1]oct-3α-yl)-4-amino-5-chloro-2-(1-ethoxyethyl-2-butynyl)oxybenzamide

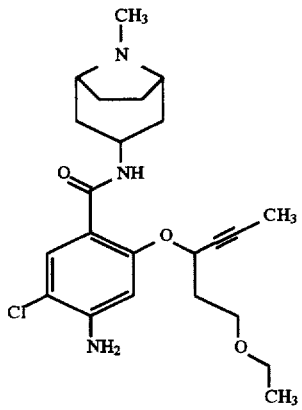

600 mg of 4-amino-5-chloro-2-[(1-ethoxyethyl-2-butynyl)oxy]benzoic acid and 490 mg of endo-3-amino-8-methyl-8-azabicyclo[3.2.1]octane were dissolved in 12 ml of pyridine, followed by the addition thereto of mg of WSC.HCl and 350 mg of 1-hydroxybenzotriazole (HOBT) at room temperature. The obtained mixture was stirred overnight and freed from the solvent by vacuum distillation. The residue was extracted with an aqueous solution of sodium hydroxide and chloroform. The organic phase was dried over anhydrous magnesium sulfate and concentrated in a vacuum. The residue was purified by silica gel column chromatography (10% methanol/chloroform) to give 630 mg of the title compound.

¹H-NMR (400 MHz, CDCl₃) δ ppm:

8.09(s, 1H), 7.98(d, J=6.2 Hz, 1H), 6.51(s, 1H) 5.05(td, J=4.9 Hz, 2.0 Hz, 1H), 4.35(s, 2H), 4.22(q, J=6.6 Hz, 1H), 3.64–3.59(m, 2H), 3.52–3.45(m, 2H), 3.16(br.s, 2H), 2.31(s, 3H), 2.32–2.23(m, 3H), 2.17–2.07(m, 3H), 1.92–1.68(m, 7H), 1.20(t, J=4.4 Hz, 3H)

EXAMPLE 42

N-(8-Methyl-8-azabicyclo[3.2.1]oct-3α-yl)-4-amino-5-chloro-2-(1-ethoxyethyl-2-butynyl)oxybenzamide hydrochloride

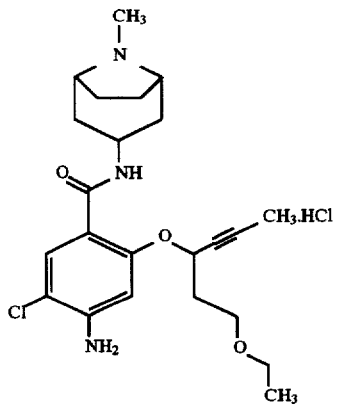

The title compound was prepared in a similar manner to that of the Example 35.

¹H-NMR (400 MHz, d₆-DMSO) δ ppm:

10.7(br.s, 1H), 7.88(d, J=4.9 Hz, 1H), 7.61(s, 1H), 6.62(s, 1H), 5.02(br.s, 1H), 3.97(m, 1H), 3.96(br.s, 2H), 3.53(t, J=6.0 Hz, 2H), 3.39(q, J=7.0 Hz, 2H), 2.61(d, J=5.1 Hz, 3H), 2.60–2.45(m, 2H), 2.29–1.94(m, 10H), 1.83(s, 3H), 1.08(t, J=7.0 Hz, 3H)

MS m/z (FAB): 434 (M⁺+1)

EXAMPLE 43

(S)-N-(3,7-Dimethyl-3,7-diazabicyclo[3.3.1]non-9-yl)-4-amino-5-chloro-2-(1-methyl)-2-butynyl)oxybenzamide

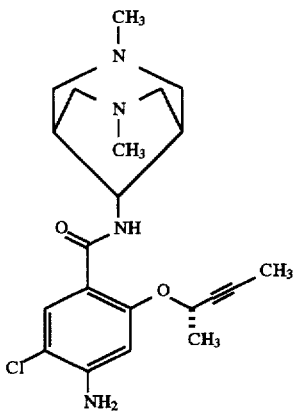

A solution of 546 mg of (S)-4-amino-5-chloro-2-[(1-methyl-2-butynyl)oxy]benzoic acid and 0.9 ml of triethylamine in 10 ml of dichloromethane was cooled with ice, followed by the addition thereto of 0.225 ml of ethyl chloroformate. The obtained mixture was stirred for 10 minutes, while the temperature was brought to room temperature. 400 mg of 9-amino-3,7-dimethyl-3,7-diazabicyclo[3.3.1]nonane was added to the resulting mixture at room temperature. The obtained mixture was stirred for 30 minutes, followed by the addition thereto of 200 mg of 9-amino-3,7-dimethyl-3,7-diazabicyclo[3.3.1]nonane at room temperature. The obtained mixture was stirred for one hour, followed by the addition thereto of dichloromethane and water. The pH of the aqueous layer was adjusted to 10 or above with a 2.5N aqueous solution of sodium hydroxide. The organic phase was recovered, dried over anhydrous magnesium sulfate, and concentrated in a vacuum. The residue was purified by silica gel column chromatography (with 0 to 10 to 20% methanol/chloroform and then with chloroform/methanol/aqueous ammonia (75/25/1.5) to give 650 mg of the title compound.

$^1$H-NMR (400 MHz, CDCl$_3$) δ ppm:

8.09(s, 1H), 8.07(d, J=8.0 Hz, 1H), 6.47(s, 1H), 4.94–4.87 (m, 1H), 4.35(s, 2H), 4.07–4.02(m, 1H), 3.01(br.d, J=10.0 Hz, 2H), 2.80(br.d, J=10.2 Hz, 2H), 2.60–2.49 (m, 2H), 2.39(br.d, J=10.0 Hz, 2H), 2.24(s, 3H), 2.23(s, 3H), 2.04(s, 2H), 1.81(s, 3H), 1.70(d, J=7.0 Hz, 3H)

EXAMPLE 44

(S)-N-(3,7-Dimethyl-3,7-diazabicyclo[3.3.1]non-9-yl)-4-amino-5-chloro-2-(1-methyl-2-butynyl)oxybenzamide hydrochloride

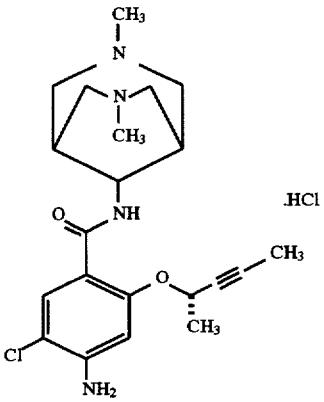

The title compound was prepared in a similar manner to that of the Example 35.

$^1$H-NMR (400 MHz, d$_6$-DMSO) δ ppm:

7.88(d, J=6.2 Hz, 1H), 7.64(s, 1H), 6.63(s, 1H), 6.05(br.s, 2H), 5.05(m, 1H), 4.07(m, 1H), 3.51–3.41(m, 2H), 3.15–3.01(m, 4H), 2.75–2.64(m, 2H), 2.55(s, 3H), 2.35 (s, 3H), 2.19(br.s, 2H), 1.82(d, J=2.0 Hz, 3H), 1.62(d, J=6.2 Hz, 3H)

MS m/z (FAB): 405 (M$^+$+1)

EXAMPLE 45

(S)-N-(Benzyl-3-pyrrolidyl)-4-amino-5-chloro-2-(1-methyl-2-butynyl)oxybenzamide

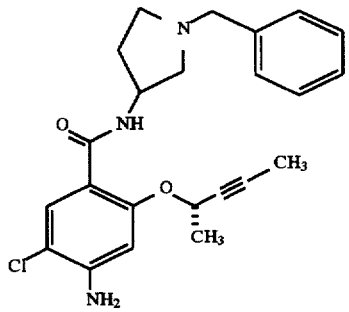

The title compound was prepared in a similar manner to that of the Example 43.

$^1$H-NMR (400 MHz, CDCl$_3$) δ ppm:

8.06(s, 1H), 8.02(d, J=7.0 Hz, 1H), 7.85–7.18(m, 5H), 4.75(s, 1H), 4.85–4.77(m, 1H), 4.63–4.54(m, 1H), 4.33 (br.s, 2H), 3.62(s+s, 2H), 2.86–2.52(m, 4H), 2.41–2.25 (m, 2H), 1.83(d+d, J=2.2 Hz, 3H), 1.65(d+d, J=6.2 Hz, 3H)

EXAMPLE 46

(S)-N-(-Benzyl-3-pyrrolidyl)-4-amino-5-chloro-2-(1-methyl-2-butynyl)oxybenzamide hydrochloride

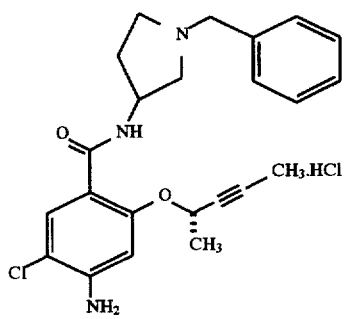

The title compound was prepared in a similar manner to that of the Example 35.

¹-NMR (400 MHz, $d_6$-DMSO) δ ppm:

10.75(br.s)+10.61(br.s) (1H), 7.96(d, J=7.0 Hz)+7.89(m) (1H), 7.60–7.40(m, 6H), 6.57(d, J=7.7 Hz)+6.55(d, J=7.7 Hz)(1H), 6.04(br.s, 2H), 4.94(m, 1H), 4.63–4.28 (m, 3H), 3.72–2.96(m, 6H), 1.82–1.77(m, 3H), 1.63–1.55(m, 3H)

MS m/z (FAB): 412 ($M^+$+1)

EXAMPLE 47

(S)-N-(3-Oxa-7-methyl-7-azabicyclo[3.3.1]non-9α- or 9β-yl)-4-amino-5-chloro-2-(1-methyl-2-butynyl)oxybenzamide

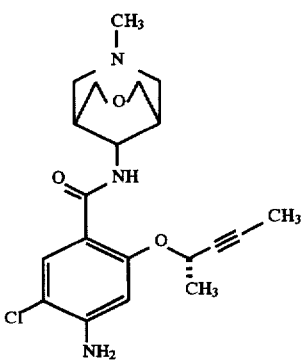

The title compound was prepared in a similar manner to that of the Example 43. The product was purified by silica gel column chromatography (10% methanol/chloroform) to give two fractions. The following fraction 1 refers to that of a shorter retention time, while the following fraction 2 refers to that of a longer retention time.

<fraction 1>

¹H-NMR (400 MHz, CDCl₃) δ ppm:

8.09(s, 1H), 8.03(d, J=6.6 Hz, 1H), 6.48(s, 1H), 5.00–4.89 (m, 1H), 4.43(br.s, 2H), 4.88–4.27(m, 1H), 4.08(d, J=11.4 Hz, 2H), 3.90(d, J=11.4 Hz, 2H), 2.94(d, J=11.7 Hz, 2H), 2.57(t, J=11.5 Hz, 2H), 2.31(s, 3H), 1.94(s, 2H), 1.83(s, 3H), 1.72(d, J=6.4 Hz, 3H)

<fraction 2>

¹H-NMR (400 MHz, CDCl₃) δ ppm:

8.27(d, J=7.3 Hz, 1H), 8.09(s, 1H), 6.47(s, 1H), 4.96–4.88 (m, 1H), 4.43(br.s, 2H), 4.20–4.13(m, 1H), 4.06–3.95 (m, 2H), 3.90(d, J=11.9 Hz, 2H), 3.14(d, J=11.4 Hz, 2H), 2.50(d, J=11.4 Hz, 2H), 2.32(s, 3H), 1.87(s, 2H), 1.84(s, 3H), 1.69(d, J=6.4 Hz, 3H)

EXAMPLE 48

(S)-N-(3-Oxa-7-methyl-7-azabicyclo[3.3.1]non-9α- or 9β-yl)-4-amino-3-chloro-2-(1-methyl-2-butynyl)oxybenzamide hydrochloride

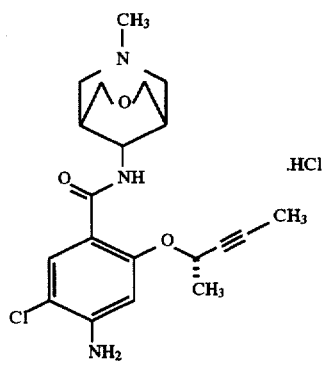

The fractions 1 and 2 prepared in the Example 47 were each treated in a similar manner to that of the Example 35 to give the title compounds.

<hydrochloride of fraction 1 of Example 47>

¹H-NMR (400 MHz, $d_6$-DMSO) δ ppm:

8.61(br.s, 1H), 7.92(d, J=5.7 Hz, 1H), 7.51(s, 1H), 6.62(s, 1H), 4.99–4.92(m, 1H), 4.17–4.11(m, 1H), 4.09(d, J=11.0 Hz, 2H), 3.90–3.48(m, 6H), 3.28–3.17(m, 2H), 2.72(d, J=4.8 Hz, 3H), 2.19(br.s, 2H), 1.82(d, J=2 Hz, 3H), 1.58(d, J=6.4 Hz, 3H )

MS m/z (FAB): 392 ($M^+$+1)

<hydrochloride of fraction 2 of Example 47>

¹H-NMR (400 MHz, $d_6$-DMSO) δ ppm:

8.71(br.s, 1H), 8.09(d, J=6.2 Hz, 1H), 7.65(s, 1H), 6.64(s, 1H), 5.11–5.03(m, 1H), 4.29–4.24(m, 1H), 4.05–3.60 (m, 8H), 3.48–3.38(m, 2H), 2.74(d, J=4.6 Hz, 3H), 2.12–2.04(m, 2H), 1.82(d, J=1.8 Hz, 3H), 1.61(d, J=6.4 Hz, 3H)

MS m/z (FAB): 392 ($M^+$+1)

EXAMPLE 49

(S)-N-(3-Ethoxy-9-methyl-9-azabicyclo[3.3.1]non-9α- (or 9β-yl) -4-amino-5-chloro-2-(1-methyl-2-butynyl)oxybenzamide

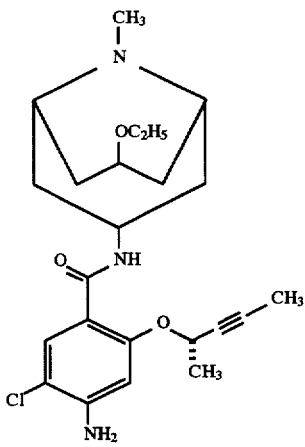

The title compounds were prepared in a similar manner to that of the Example 43. The product was subjected to HPLC with a chiral column (Chiralcel OJ, a product of Daicel Chemical Industries, Ltd.) and eluted with a mobile phase comprising ethanol, hexane and triethylamine at a ratio of 9:1:0.01 to give two fractions. The following fraction 1 refers to that of a shorter retention time, while the following fraction 2 refers to that of a longer retention time.

<fraction 1>

$^1$H-NMR (400 MHz, CDCl$_3$) δ ppm:

8.55(s, 1H), 7.60(d, J=7.7 Hz, 1H), 6.46(s, 1H), 4.86–4.79 (m, 1H), 4.48–4.32(m, 3H), 4.01(quint., J=8.6 Hz, 1H), 3.55(q, J=7.1 Hz, 2H), 3.08(br.s, 2H), 2.51(s, 3H), 2.03(td, J=5.9, 14.8 Hz, 2H), 1.95–1.81(m, 5H), 1.80–1.64(m, 7H), 1.20(t, J=7.1 Hz, 3H)

<fraction 2>

$^1$-NMR (400 MHz, CDCl$_3$) δ ppm:

8.07(s, 1H), 7.57(d, J=7.1 Hz, 1H), 6.48(s, 1H), 4.88–4.80 (m, 1H), 4.40–4.29(m, 3H), 3.89–3.78(m, 1H), 3.50(q, J=7.1 Hz, 2H), 3.21(br.d, J=9.6 Hz, 2H), 2.64–2.50(m, 2H), 2.42(s, 3H), 1.85(s, 3H), 1.81–1.55(m, 9H), 1.20 (t, J=7.1 Hz, 3H)

EXAMPLE 50

(S)-N-(3-Ethoxy-9-methyl-9-azabicyclo[3.3.1]non-9α- or 9β-yl)-4-amino-5-chloro-2-(1-methyl-2-butynyl)oxybenzamide hydrochloride

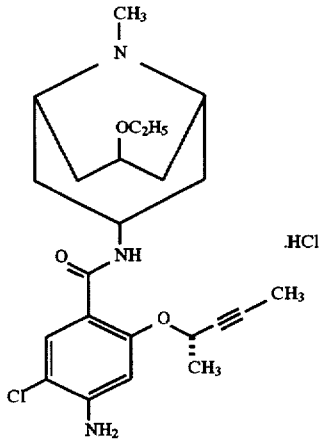

The fractions 1 and 2 prepared in the Example 49 were each treated in a similar manner to that of the Example 35 to give the title compounds.

<hydrochloride of fraction 1 of Example 49>

$^1$H-NMR (400 MHz, d$_6$-DMSO) δ ppm:

11.08(br.s)+10.66(br.s)(1H), 7.71(d, J=7.3 Hz)+7.63(d, J=3 Hz), (1H), 7.66(s)+7.55(s)(1H), 6.59(s, 1H), 5.02–4.87(m, 1H), 4.38–4.20(m, 1H), 4.04–3.90(m, 1H), 3.62(br.s, 2H), 3.54–3.35(m, 4H), 2.86(d, J=4.9 Hz)+2.79(d, J=4.9 Hz)(3H), 2.31–1.84(m, 8H), 1.82(s, 3H), 1.65(d, J=6.4 Hz)+1.60(d, J=6.4 Hz)(3H), 1.07(t, J=7 Hz, 3H)

MS m/z (FAB): 434 (M$^+$+1)

<hydrochloride of fraction 2 of Example 49>

$^1$H-NMR (400 MHz, d$_6$-DMSO) δ ppm:

0.67(br.s)+9.76(br.s)(1H), 7.83(d, J=6.6 Hz)+7.67(d, J=6.6 Hz)(1H), 7.66(s)+(7.60(s)(1H), 6.61(s)+6.59(s) (1H), 5.04–4.90(m, 1H), 4.40–4.03(m, 2H), 3.74–3.32 (m, 6H), 2.78(d, J=4.8 Hz, 3H), 2.61–2.45(m, 2H), 2.16–1.66(m, 9H), 1.53(d, J=6.2 Hz)+1.52(d, J=6.2 Hz)(3H), 1.09(t, J=7.0 Hz)+1.03(t, J=7.0 Hz)(3H)

MS m/z (FAB): 434 (M$^+$+1)

EXAMPLE 51

(S)-N-(8-Methyl-8-azabicyclo[3.2.1]oct2α- or 2β-yl)-4-amino-5-chloro-2-(1-methyl-2-butynyl)oxybenzamide

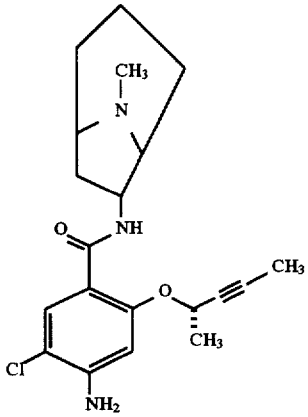

500 mg of (S)-4-amino-5-chloro-2-[(1-methyl-2-butynyl)oxy]benzoic acid and 553 mg of 2-amino-8-methyl-5-azabicyclo[3.2.1]octane were dissolved in 5 ml of pyridine, followed by the addition thereto of 812 mg of dicyclohexylcarbodiimide (DCC) at room temperature. The obtained mixture was stirred overnight, followed by the addition thereto of 5 ml of water. Insolubles were filtered out and the filtrate as basified with an aqueous solution of sodium hydroxide and extracted with chloroform. The organic phase was dried over anhydrous magnesium sulfate and freed from the solvent by distillation. The residue was purified by silica gel column chromatography (0 to 3 to 6 to 10 to 20 to 80% methanol/chloroform) to give the title compounds as two fractions (fraction 1:270 mg, fraction 2:260 mg). The fraction 1 refers to that of a shorter retention time, while the fraction 2 refers to that of a longer retention time.

<fraction 1>

$^1$-NMR (400 MHz, CDCl$_3$) δ ppm:

8.08(s, 1H), 8.04(d, J=6.6 Hz, 1H), 6.47(s, 1H), 4.88–4.81 (m, 1H), 4.49–4.40(m, 1H), 4.38(s, 2H), 3.39–3.31(m, 1H), 3.15–3.10(m, 1H), 2.55(s, 3H), 2.33–2.24(m, 1H), 2.01–1.76(m, 8H), 1.70–1.64(m, 3H), 1.64–1.48(m, 3H), 1.28–1.18(m, 1H)

<fraction 2>

$^1$H-NMR (400 MHz, CDCl$_3$) δ ppm:

8.13(s, 1H), 8.04–7.97(m, 1H), 6.49(s)+6.47(s)(1H), 4.96–4.80(m, 2H), 4.39(s, 2H), 3.40–3.32(m, 1H), 3.24–3.18(m, 1H), 2.83–2.70(m, 1H), 2.48(s, 8H), 1.92–1.71(m, 4H), 1.70–1.50(m, 7H), 1.45–1.34(m, 2H)

EXAMPLE 52

Resolution of diastereomers of fraction 2 of Example 2

The fraction 2 (740 mg) of the Example 51 was subjected to HPLC with a chiral cel (Chiralcel OD, a product of Daicel Chemical Industries, Ltd.) and eluted with a mobile phase comprising ethanol, hexane and triethylamine at a ratio of 10:90:0.5 to give two fractions (fraction 2-1: 280 mg, fraction 2-2: 110 mg). The fraction 2-1 refers to that of a shorter retention time and the fraction 2-2 refers to that of a longer retention time.

<fraction 2-1>

$^1$H-NMR (400 MHz, CDCl$_3$) δ ppm:

8.13(s, 1H), 8.01(d, J=6.8 Hz, 1H), 6.49(s, 1H), 4.96–4.88 (m, 1H), 4.88–4.78(m, 1H), 4.37(s, 2H), 3.32–3.27(m, 1H), 3.17–3.12(m, 1H), 2.80–2.69(m, 1H), 2.44(s, 3H), 1.98–1.85(m, 1H), 1.84–1.75(m, 4H), 1.73–1.51(m, 6H), 1.43–1.30(m, 2H)

MS m/z (FAB): 376 (M$^+$+1)

<fraction 2-2>

$^1$-NMR (400 MHz, CDCl$_3$) δ ppm:

8.13(s, 1H), 7.99(d, J=6.9 Hz, 1H), 6.47(s, 1H), 4.95–4.88 (m, 1H), 4.88–4.79(m, 1H), 4.37(s, 2H), 3.34–3.28(m, 1H), 3.18–3.12(m, 1H), 2.80–2.69(m, 1H), 2.44(s, 3H), 1.95–1.84(m, 1H), 1.85(d, J=2.0 Hz, 3H), 1.80–1.70(m, 1H), 1.71–1.46(m, 6H), 1.42–1.35(m, 2H)

MS m/z (FAB): 376 (M$^+$+1)

EXAMPLE 53

(S)-N-(8-Methyl-8-azabicyclo[3.2.1]oct-2α- or 2β-yl)-4-amino-5-chloro-2-(1-methyl-2-butynyl)oxybenzamide hydrochloride

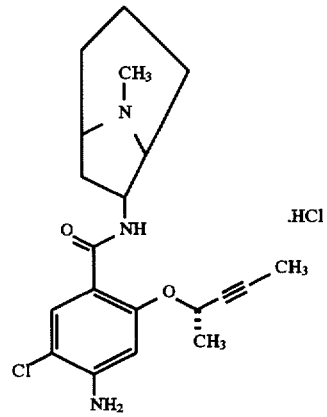

The fractions 1 and 2 prepared in the Example 51 and the fractions 2-1 and 2-2 prepared in the Example 52 were each treated in a similar manner to that of the Example 35 to give the title compounds.

<hydrochloride of fraction 1 of Example 51>

$^1$-NMR (400 MHz, d$_6$-DMSO) δ ppm:

8.02–7.94, 7.93(m+d, J=4.7 Hz, 1H), 7.66, 7.62, 7.54, 7.53(s×4, 1H), 6.61, 6.59, 6.58, 6.56(s×4, 1H), 6.10–5.90(m, 2H), 5.01–4.91(m, 1H), 4.46–4.27(m, 1H), 4.04–3.96(m, 1H), 3.90–3.81(m, 1H), 3.41–3.33 (m, 1H), 2.88–2.75(m, 3H), 2.05–1.90(m, 2H), 1.85–1.76(m, 3H), 1.70–1.34(m, 8H)

MS m/z (FAB): 376 (M$^+$+1)

<hydrochloride of fraction 2 of Example 51>

$^1$-NMR (400 MHz, d$_6$-DMSO) δ ppm:

9.90(br.s, 1H), 8.01, 7.99(d×2, J=5.7 Hz, 1H), 7.61+7.58 (s×2, 1H), 6.60(s, 1H), 6.05(br.s, 2H), 5.08–4.99(m,

1H), 4.83–4.71(m, 1H), 3.98–3.91(m, 1H), 3.87–3.81 (m, 1H), 3.35–3.30(m, 1H), 2.86, 2.78(d×2, J=5.1 Hz, 3H), 2.14–1.87(m, 2H), 1.83, 1.80(d×2, J=1.8 Hz, 3H), 1.74–1.62(m, 4H), 1.61–1.48(m, 4H)
MS m/z (FAB): 376 (M$^+$+1)

<hydrochloride of fraction 2-1 of Example 52>

$^1$H-NMR (400 MHz, d$_6$-DMSO) δ ppm:

9.81(br.s, 1H), 8.01(d, J=5.7 Hz, 1H), 7.58(s, 1H), 6.61(s, 1H), 6.04(s, 2H), 5.08–5.00(m 1H), 4.81–4.71(m, 1H), 3.98–3.78(m, 2H), 3.32–3.30(m, 1H), 2.78(d, J=5.0 Hz, 3H), 2.11–1.87(m, 2H), 1.81(d, J=1.8 Hz, 3H), 1.77–1.62(m, 4H), 1.61–1.46(m, 4H)
MS m/z (FAB): 376 (M$^+$+1)
$[α]_D^{23}$=–115.2° (C=1.0, MeOH)

<hydrochloride of fraction 2-2 of Example 52>

$^1$H-NMR (400 MHz, d$_6$-DMSO) δ ppm:

9.76(s, 1H), 7.99(d, J=5.7 Hz, 1H), 7.61(s, 1H), 6.60(s, 1H), 6.06(s, 2H), 5.09–5.00(m, 1H), 4.82–4.72 (m, 1H), 3.98–3.91(m, 1H), 3.89–3.81(m, 1H), 3.35–3.30 (m, 1H), 2.86(d, J=5.1 Hz, 3H), 2.06–1.85(m, 2H), 1.83(d, J=1.8 Hz, 3H), 1.75–1.63(m, 4H), 1.61–1.50(m, 4H)
MS m/z (FAB): 376 (M$^+$+1)
$[α]_D^{23}$=–80.3° (C=1.0, MeOH)

EXAMPLE 54

(S)-N-(1-Azatricyclo[3.3.1.1$^{3,7}$]dec-10-yl)-4-amino-5-chloro-(1-methyl-2-butynyl)oxybenzamide

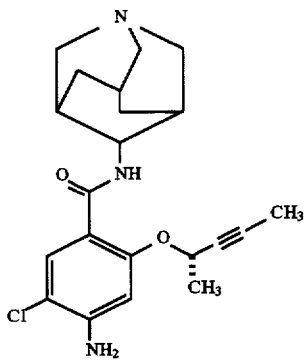

The title compound was prepared in a similar manner to that of the Example 43.

$^1$H-NMR (400 MHz, CDCl$_3$) δ ppm:

8.09(d, J=5.7 Hz, 1H), 8.04(s, 1H), 6.51(s, 1H), 4.99–4.91 (m, 1H), 4.54(s, 2H), 4.36–4.30(m, 1H), 3.62–3.55(m, 2H), 3.49–3.45(m, 2H), 3.41–3.35(m, 2H), 2.48–2.42 (m, 2H), 2.31–2.26(m, 1H), 2.11–2.08 (m, 4H), 1.88(d, J=2.0 Hz, 3H), 1.70(d, J=6.4 Hz, 3H)

EXAMPLE 55

(S)-N-(1-Azatricyclo[3.3.1.1$^{3,7}$]dec-10-yl)-4-amino-5-chloro-(1-methyl-2-butynyl)oxybenzamide hydrochloride

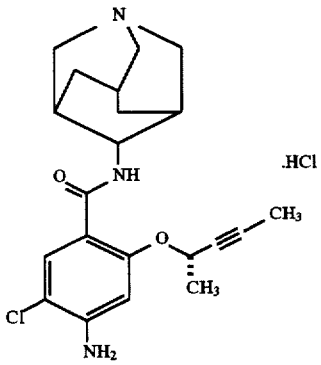

The title compound was prepared in a similar manner to that of the Example 35.

$^1$H-NMR (400 MHz, d$_6$-DMSO) δ ppm:

10.69(s, 1H), 7.93(d, J=6.0 Hz, 1H), 7.54(s, 1H), 6.61(s, 1H), 5.80(br.s, 2H), 5.00–4.92(m, 1H), 4.01–4.04(m, 1H), 3.94–3.54(m, 6H), 2.25–2.17(m, 2H), 2.09–1.99 (m, 3H), 1.93–1.85(m, 2H), 1.83(d, J=1.8 Hz, 8H), 1.59(d, J=6.4 Hz, 3H)
MS m/z (FAB): 388 (M$^+$+1)

We claim:

1. An aminobenzoic acid derivative represented by the following general formula (I) or a pharmacologically acceptable salt thereof:

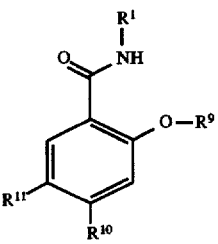

(I)

wherein R$^1$ represents a group represented by the formula:

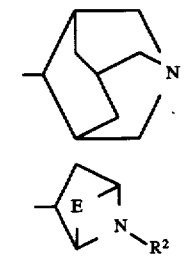

E is a group represented by formula —(CH$_2$)$_3$— or a group represented by formula —O—(CH$_2$)$_2$; R$^2$ represents hydrogen, lower alkyl or arylalkyl;

R$^9$ represents alkynyl;

R$^{10}$ represents amino, acylamino or alkylamino; and

R$^{11}$ represents halogen.

2. An aminobenzoic acid or a pharmacologically acceptable salt thereof as set forth in claim 1, wherein R$^9$ is a group represented by the formula:

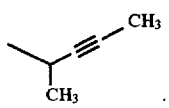

3. An aminobenzoic acid or a pharmacologically acceptable salt thereof as set forth in claim 1, wherein $R^{10}$ is amino and $R^{11}$ is chlorine.

4. An aminobenzoic acid or a pharmacologically acceptable salt thereof as set forth in claim 2, wherein $R^{10}$ is amino and $R^{11}$ is chloride.

5. The compound as claimed in claim 1, which is an (R) or (S) isomer or a pharamacoligically acceptable salt thereof.

6. A pharmacological composition comprising a pharmacologically effective amount of the compound as defined in claim 1 or a pharmacologically acceptable salt thereof and a pharmacologically acceptable carrier.

7. A method for preventing or therapeutically treating a disease against which serotonin antagonism or an acetylcholine release accelerating action is efficacious by administering a pharmacologically effective amount of the compound as defined in claim 1 to a subject who suffers or will suffer from the disease.

8. The method as claimed in claim 7, in which a gastrointestinal function is increased.

9. The method as claimed in claim 7, in which an antiemetic or an oxiolytic is effective or an irritable bowel syndrome is prevented or treated.

* * * * *